US008425757B2

(12) United States Patent
Wu et al.

(10) Patent No.: US 8,425,757 B2
(45) Date of Patent: *Apr. 23, 2013

(54) GATED AMPEROMETRY

(75) Inventors: Huan-Ping Wu, Granger, IN (US);
Christine D. Nelson, Edwardsburg, MI
(US); Greg P. Beer, Cassopolis, MI (US)

(73) Assignee: Bayer HealthCare LLC, Tarrytown, NY (US)

(*) Notice: Subject to any disclaimer, the term of this patent is extended or adjusted under 35 U.S.C. 154(b) by 1434 days.

This patent is subject to a terminal disclaimer.

(21) Appl. No.: 11/960,062

(22) Filed: Dec. 19, 2007

(65) Prior Publication Data
US 2008/0173552 A1    Jul. 24, 2008

Related U.S. Application Data

(63) Continuation of application No. PCT/US2006/028013, filed on Jul. 19, 2006.

(60) Provisional application No. 60/746,771, filed on May 8, 2006, provisional application No. 60/700,787, filed on Jul. 20, 2005.

(51) Int. Cl.
*G01N 27/327* (2006.01)

(52) U.S. Cl.
USPC .......... 205/792; 204/403.02; 205/777.5

(58) Field of Classification Search .......... 204/400, 204/403.01, 403.02, 406, 408; 205/775, 205/777.5, 792
See application file for complete search history.

(56) References Cited

U.S. PATENT DOCUMENTS

| 3,420,205 A | 1/1969 | Morrison |
| 3,505,136 A | 4/1970 | Attwood |
| 3,510,268 A | 5/1970 | Hach |
| 3,551,295 A | 12/1970 | Dyer |
| 3,573,139 A | 3/1971 | Mori et al. |
| 3,621,381 A | 11/1971 | Eckfeldt |
| 3,690,836 A | 9/1972 | Buissiere et al. |
| 3,715,192 A | 2/1973 | Wenz et al. |

(Continued)

FOREIGN PATENT DOCUMENTS

| CA | 2423837 | 10/2000 |
| CA | 2358993 | 5/2001 |

(Continued)

OTHER PUBLICATIONS

Parkes, et al., "Balancing Test Time with accurancy and Percision in blood glucose monitoring How fast is too fast?", Jun. 2003.

(Continued)

*Primary Examiner* — Kaj K Olsen
(74) *Attorney, Agent, or Firm* — Blanchard & Associates

(57) ABSTRACT

A sensor system, device, and methods for determining the concentration of an analyte in a sample is described. Gated amperometric pulse sequences including multiple duty cycles of sequential excitations and relaxations may provide a shorter analysis time and/or improve the accuracy and/or precision of the analysis. The disclosed gated amperometric pulse sequences may reduce analysis errors arising from the hematocrit effect, variance in cap-gap volumes, non-steady-state conditions, mediator background, under-fill, temperature changes in the sample, and a single set of calibration constants.

24 Claims, 12 Drawing Sheets

U.S. PATENT DOCUMENTS

| | | |
|---|---|---|
| 3,720,093 A | 3/1973 | Gill |
| 3,763,422 A | 10/1973 | MacPhee et al. |
| 3,770,607 A | 11/1973 | Williams |
| 3,776,832 A | 12/1973 | Oswin et al. |
| 3,791,933 A | 2/1974 | Moyer et al. |
| 3,838,033 A | 9/1974 | Mindt et al. |
| 3,902,970 A | 9/1975 | Levin |
| 3,917,453 A | 11/1975 | Milligan et al. |
| 3,919,627 A | 11/1975 | Allen |
| 3,925,183 A | 12/1975 | Oswin et al. |
| 3,937,615 A | 2/1976 | Clack et al. |
| 3,948,745 A | 4/1976 | Guilbault et al. |
| 3,980,437 A | 9/1976 | Kishimoto et al. |
| 4,005,002 A | 1/1977 | Racine et al. |
| 4,008,448 A | 2/1977 | Muggli |
| 4,040,908 A | 8/1977 | Clark, Jr. |
| 4,053,381 A | 10/1977 | Hamblen et al. |
| 4,065,263 A | 12/1977 | Woodbridge et al. |
| 4,077,861 A | 3/1978 | Lauer |
| 4,123,701 A | 10/1978 | Josefsen et al. |
| 4,127,448 A | 11/1978 | Schick et al. |
| 4,137,495 A | 1/1979 | Brown |
| 4,184,936 A | 1/1980 | Paul et al. |
| 4,214,968 A | 7/1980 | Battaglia et al. |
| 4,217,196 A | 8/1980 | Huch |
| 4,224,125 A | 9/1980 | Nakamura et al. |
| 4,225,410 A | 9/1980 | Pace et al. |
| 4,229,426 A | 10/1980 | Haagensen, Jr. |
| 4,230,537 A | 10/1980 | Delente et al. |
| 4,233,029 A | 11/1980 | Columbus |
| 4,260,680 A | 4/1981 | Muramatsu et al. |
| 4,263,343 A | 4/1981 | Kim |
| 4,265,250 A | 5/1981 | Parker |
| 4,273,639 A | 6/1981 | Gottermeier |
| 4,297,184 A | 10/1981 | Dyer |
| 4,297,569 A | 10/1981 | Flies |
| 4,301,412 A | 11/1981 | Hill et al. |
| 4,303,887 A | 12/1981 | Hill et al. |
| 3,562,041 A | 2/1982 | Arthur |
| 4,323,536 A | 4/1982 | Columbus |
| 4,329,642 A | 5/1982 | Luthi et al. |
| 4,366,033 A | 12/1982 | Richter et al. |
| 4,376,689 A | 3/1983 | Nakamura et al. |
| 4,381,775 A | 5/1983 | Nose et al. |
| 4,396,464 A | 8/1983 | Giner et al. |
| 4,402,940 A | 9/1983 | Nose et al. |
| 4,403,984 A | 9/1983 | Ash et al. |
| 4,407,290 A | 10/1983 | Wilber |
| 4,407,959 A | 10/1983 | Tsuji et al. |
| 4,413,407 A | 11/1983 | Columbus |
| 4,420,564 A | 12/1983 | Tsuji et al. |
| 4,431,004 A | 2/1984 | Bessman et al. |
| 4,436,094 A | 3/1984 | Cerami |
| 4,440,175 A | 4/1984 | Wilkins |
| 4,473,457 A | 9/1984 | Columbus |
| 4,476,149 A | 10/1984 | Poppe et al. |
| 4,477,314 A | 10/1984 | Richter et al. |
| 4,477,575 A | 10/1984 | Vogel et al. |
| 4,490,216 A | 12/1984 | McConnell |
| 4,499,423 A | 2/1985 | Matthiessen |
| 4,502,938 A | 3/1985 | Covington et al. |
| 4,517,291 A | 5/1985 | Seago |
| 4,545,382 A | 10/1985 | Higgins et al. |
| 4,547,735 A | 10/1985 | Kiesewetter et al. |
| 4,552,458 A | 11/1985 | Lowne |
| 4,561,944 A | 12/1985 | Sasaki et al. |
| 4,571,292 A | 2/1986 | Liu et al. |
| 4,578,716 A | 3/1986 | van Rijckevorsel et al. |
| 4,579,893 A | 4/1986 | Wang et al. |
| 4,582,684 A | 4/1986 | Vogel et al. |
| 4,591,550 A | 5/1986 | Hafeman et al. |
| 4,628,193 A | 12/1986 | Blum |
| 4,642,295 A | 2/1987 | Baker |
| 4,648,665 A | 3/1987 | Davis et al. |
| 4,652,830 A | 3/1987 | Brown |
| 4,654,197 A | 3/1987 | Lilja et al. |
| 4,671,288 A | 6/1987 | Gough |
| 4,676,653 A | 6/1987 | Strohmeier et al. |
| 4,679,562 A | 7/1987 | Luksha |
| 4,680,268 A | 7/1987 | Clark |
| 4,682,602 A | 7/1987 | Prohaska |
| 4,686,479 A | 8/1987 | Young et al. |
| 4,703,017 A | 10/1987 | Campbell et al. |
| 4,703,756 A | 11/1987 | Gough et al. |
| 4,713,347 A | 12/1987 | Mitchell et al. |
| 4,714,874 A | 12/1987 | Morris et al. |
| 4,721,677 A | 1/1988 | Clark |
| 4,731,726 A | 3/1988 | Allen et al. |
| 4,734,184 A | 3/1988 | Burleigh et al. |
| 4,745,076 A | 5/1988 | Muller et al. |
| 4,746,607 A | 5/1988 | Mura et al. |
| 4,750,496 A | 6/1988 | Reinhart et al. |
| 4,759,828 A | 7/1988 | Young et al. |
| 4,789,804 A | 12/1988 | Karube et al. |
| 4,795,542 A | 1/1989 | Ross et al. |
| 4,797,256 A | 1/1989 | Watlington, IV |
| 4,805,624 A | 2/1989 | Yao et al. |
| 4,806,311 A | 2/1989 | Greenquist |
| 4,806,312 A | 2/1989 | Greenquist |
| 4,810,203 A | 3/1989 | Komatsu |
| 4,816,224 A | 3/1989 | Vogel et al. |
| 4,820,399 A | 4/1989 | Senda et al. |
| 4,820,636 A | 4/1989 | Hill et al. |
| 4,830,959 A | 5/1989 | McNeil et al. |
| 4,832,814 A | 5/1989 | Root |
| 4,834,234 A | 5/1989 | Sacherer et al. |
| 4,849,330 A | 7/1989 | Humphries et al. |
| 4,854,153 A | 8/1989 | Miyagawa et al. |
| 4,865,873 A | 9/1989 | Cole, Jr. et al. |
| 4,877,580 A | 10/1989 | Aronowitz et al. |
| 4,894,137 A | 1/1990 | Takizawa et al. |
| 4,897,162 A | 1/1990 | Lewandowski et al. |
| 4,919,770 A | 4/1990 | Preidel et al. |
| 4,927,516 A | 5/1990 | Yamaguchi et al. |
| 4,929,330 A | 5/1990 | Osaka et al. |
| 4,929,545 A | 5/1990 | Freitag |
| 4,935,105 A | 6/1990 | Churchouse |
| 4,936,106 A | 6/1990 | Beach, Jr. et al. |
| 4,936,346 A | 6/1990 | Kugler |
| 4,938,860 A | 7/1990 | Wogoman |
| 4,940,945 A | 7/1990 | Littlejohn et al. |
| 4,954,087 A | 9/1990 | Lauks et al. |
| 4,956,275 A | 9/1990 | Zuk et al. |
| 4,963,814 A | 10/1990 | Parks et al. |
| 4,970,145 A | 11/1990 | Bennetto et al. |
| 4,975,647 A | 12/1990 | Downer et al. |
| 4,976,724 A | 12/1990 | Nieto |
| 4,994,167 A * | 2/1991 | Shults et al. ............ 204/403.05 |
| 4,999,582 A | 3/1991 | Parks et al. |
| 4,999,632 A | 3/1991 | Parks |
| 5,018,164 A | 5/1991 | Brewer et al. |
| 5,019,974 A | 5/1991 | Beckers |
| 5,035,862 A | 7/1991 | Dietze et al. |
| 5,039,618 A | 8/1991 | Stone |
| 5,046,618 A | 9/1991 | Wood |
| 5,049,487 A | 9/1991 | Phillips et al. |
| 5,057,477 A | 10/1991 | Becker et al. |
| 5,059,199 A | 10/1991 | Okada et al. |
| 5,059,394 A | 10/1991 | Phillips et al. |
| 5,066,372 A | 11/1991 | Weetall |
| 5,075,077 A | 12/1991 | Durley, III et al. |
| 5,096,669 A | 3/1992 | Lauks et al. |
| 5,108,564 A | 4/1992 | Szuminsky et al. |
| 5,108,819 A | 4/1992 | Heller et al. |
| 5,112,455 A | 5/1992 | Cozzette et al. |
| 5,112,758 A | 5/1992 | Fellman et al. |
| 5,118,183 A | 6/1992 | Cargill et al. |
| 5,120,420 A | 6/1992 | Nankai et al. |
| 5,120,421 A | 6/1992 | Glass et al. |
| 5,122,244 A | 6/1992 | Hoenes et al. |
| 5,128,015 A | 7/1992 | Szuminsky et al. |
| 5,131,999 A * | 7/1992 | Gunasingham ......... 204/403.02 |
| 5,140,176 A | 8/1992 | Okino |
| 5,141,850 A | 8/1992 | Cole et al. |
| 5,141,868 A | 8/1992 | Shanks et al. |
| 5,143,694 A | 9/1992 | Schafer et al. |
| 5,179,005 A | 1/1993 | Phillips et al. |

| | | | | | |
|---|---|---|---|---|---|
| 5,179,288 A | 1/1993 | Miffitt et al. | 5,508,200 A | 4/1996 | Tiffany et al. |
| 5,182,707 A | 1/1993 | Cooper et al. | 5,508,203 A | 4/1996 | Fuller et al. |
| 5,187,100 A | 2/1993 | Matzinger et al. | 5,509,410 A | 4/1996 | Hill et al. |
| 5,192,415 A | 3/1993 | Yosioka et al. | 5,512,159 A | 4/1996 | Yoshioka et al. |
| 5,202,261 A | 4/1993 | Musho et al. | 5,515,847 A | 5/1996 | Braig et al. |
| 5,217,594 A | 6/1993 | Henkens et al. | 5,520,786 A | 5/1996 | Bloczynski et al. |
| 5,220,920 A | 6/1993 | Gharib | 5,526,111 A | 6/1996 | Collins et al. |
| 5,223,117 A | 6/1993 | Wrighton et al. | 5,526,120 A | 6/1996 | Jina et al. |
| 5,229,282 A | 7/1993 | Yoshioka et al. | 5,526,808 A | 6/1996 | Kaminsky |
| 5,232,516 A | 8/1993 | Hed | 5,532,128 A | 7/1996 | Eggers et al. |
| 5,232,667 A | 8/1993 | Hieb et al. | 5,552,116 A | 9/1996 | Yokota et al. |
| 5,232,668 A | 8/1993 | Grante et al. | 5,554,269 A | 9/1996 | Joseph et al. |
| 5,234,813 A | 8/1993 | McGeehan et al. | 5,554,531 A | 9/1996 | Zweig |
| 5,243,516 A | 9/1993 | White | 5,556,789 A | 9/1996 | Goerlach-Graw et al. |
| 5,246,858 A | 9/1993 | Arbuckle et al. | 5,563,031 A | 10/1996 | Yu |
| 5,250,439 A | 10/1993 | Musho et al. | 5,563,042 A | 10/1996 | Phillips et al. |
| 5,261,411 A | 11/1993 | Hughes | 5,569,591 A | 10/1996 | Kell et al. |
| 5,262,035 A | 11/1993 | Gregg et al. | 5,569,608 A | 10/1996 | Sommer |
| 5,264,103 A | 11/1993 | Yoshioka et al. | 5,572,159 A | 11/1996 | McFarland |
| 5,266,179 A | 11/1993 | Nanki et al. | 5,575,403 A | 11/1996 | Charlton et al. |
| 5,269,891 A | 12/1993 | Colin | 5,575,895 A | 11/1996 | Ikeda et al. |
| 5,279,294 A | 1/1994 | Anderson et al. | 5,576,073 A | 11/1996 | Kickelhain |
| 5,281,395 A | 1/1994 | Markart et al. | 5,580,794 A | 12/1996 | Allen |
| 5,282,950 A | 2/1994 | Dietze et al. | 5,589,045 A | 12/1996 | Hyodo |
| 5,284,770 A | 2/1994 | Adrain et al. | 5,589,326 A | 12/1996 | Deng et al. |
| 5,286,362 A | 2/1994 | Hoenes et al. | 5,593,390 A | 1/1997 | Castellano et al. |
| 5,288,636 A | 2/1994 | Pollmann et al. | 5,593,739 A | 1/1997 | Kickelhain |
| 5,304,468 A | 4/1994 | Phillips et al. | 5,594,906 A | 1/1997 | Holmes, II et al. |
| 5,306,623 A | 4/1994 | Kiser et al. | 5,597,532 A | 1/1997 | Connolly |
| 5,311,426 A | 5/1994 | Donohue et al. | 5,603,820 A | 2/1997 | Christodoulou et al. |
| 5,312,590 A | 5/1994 | Gunasingham | 5,604,110 A | 2/1997 | Baker et al. |
| 5,320,732 A | 6/1994 | Nankai et al. | 5,605,662 A | 2/1997 | Heller et al. |
| 5,332,479 A | 7/1994 | Uenoyama et al. | 5,605,837 A | 2/1997 | Karimi et al. |
| 5,334,296 A | 8/1994 | Henkens et al. | 5,611,909 A | 3/1997 | Studer |
| 5,344,754 A | 9/1994 | Zweig | 5,620,579 A | 4/1997 | Genshaw et al. |
| 5,352,351 A | 10/1994 | White et al. | 5,620,863 A | 4/1997 | Tomasco et al. |
| 5,353,351 A | 10/1994 | Bartoli et al. | 5,620,890 A | 4/1997 | Kamps-Holtzapple et al. |
| 5,354,447 A | 10/1994 | Uenoyama et al. | 5,628,890 A | 5/1997 | Carter et al. |
| 5,366,609 A | 11/1994 | White et al. | 5,630,986 A | 5/1997 | Charlton et al. |
| 5,368,707 A | 11/1994 | Henkens et al. | 5,635,362 A | 6/1997 | Levine et al. |
| 5,371,687 A | 12/1994 | Holmes, II et al. | 5,635,364 A | 6/1997 | Clark et al. |
| 5,376,254 A | 12/1994 | Fisher | 5,639,671 A | 6/1997 | Bogart et al. |
| 5,379,214 A | 1/1995 | Arbuckle et al. | 5,642,734 A | 7/1997 | Ruben et al. |
| 5,384,028 A | 1/1995 | Ito | 5,644,501 A | 7/1997 | Lin et al. |
| 5,385,846 A | 1/1995 | Kuhn et al. | 5,645,798 A | 7/1997 | Schreiber et al. |
| 5,389,215 A | 2/1995 | Horiuchi et al. | 5,650,061 A | 7/1997 | Kuhr et al. |
| 5,391,272 A | 2/1995 | O'Daly et al. | 5,650,062 A | 7/1997 | Ikeda et al. |
| 5,393,903 A | 2/1995 | Gratzel et al. | 5,653,863 A | 8/1997 | Genshaw et al. |
| 5,395,504 A | 3/1995 | Saurer et al. | 5,654,178 A | 8/1997 | Fitzpatrick et al. |
| 5,403,462 A | 4/1995 | Lev et al. | 5,656,502 A | 8/1997 | Mackay et al. |
| 5,405,511 A | 4/1995 | White et al. | 5,658,443 A | 8/1997 | Yamamoto et al. |
| 5,410,059 A | 4/1995 | Fraser et al. | 5,658,802 A | 8/1997 | Hayes et al. |
| 5,410,474 A | 4/1995 | Fox | 5,660,791 A | 8/1997 | Brenneman et al. |
| 5,411,647 A | 5/1995 | Johnson et al. | 5,665,215 A | 9/1997 | Bussmann et al. |
| 5,413,690 A | 5/1995 | Kost et al. | 5,670,031 A | 9/1997 | Hintsche et al. |
| 5,413,764 A | 5/1995 | Haar | 5,682,884 A | 11/1997 | Hill et al. |
| 5,418,142 A | 5/1995 | Kiser et al. | 5,686,659 A | 11/1997 | Neel et al. |
| 5,421,189 A | 6/1995 | Dussault | 5,691,486 A | 11/1997 | Behringer et al. |
| 5,424,035 A | 6/1995 | Hones et al. | 5,691,633 A | 11/1997 | Liu et al. |
| 5,426,032 A | 6/1995 | Phillips et al. | 5,695,623 A | 12/1997 | Michel et al. |
| 5,427,912 A | 6/1995 | Brown et al. | 5,698,083 A | 12/1997 | Glass |
| 5,429,735 A | 7/1995 | Johnson et al. | 5,700,695 A | 12/1997 | Yassinzadeh et al. |
| 5,437,772 A | 8/1995 | DeCastro et al. | 5,704,354 A | 1/1998 | Preidel et al. |
| 5,437,999 A | 8/1995 | Diebold et al. | 5,708,247 A | 1/1998 | McAleer et al. |
| 5,438,271 A | 8/1995 | White et al. | 5,710,011 A | 1/1998 | Forrow et al. |
| 5,439,826 A | 8/1995 | Kontorovich | 5,710,622 A | 1/1998 | Neel et al. |
| 5,445,967 A | 8/1995 | Deuter | 5,719,667 A | 2/1998 | Miers |
| 5,447,837 A | 9/1995 | Urnovitz | 5,720,862 A | 2/1998 | Hamamoto et al. |
| 5,453,360 A | 9/1995 | Yu | 5,723,284 A | 3/1998 | Ye |
| 5,468,366 A | 11/1995 | Wegner et al. | 5,723,345 A | 3/1998 | Yamauchi et al. |
| 5,469,846 A | 11/1995 | Khan | 5,727,548 A | 3/1998 | Hill et al. |
| 5,470,533 A | 11/1995 | Shindo et al. | 5,728,074 A | 3/1998 | Castellano et al. |
| 5,477,326 A | 12/1995 | Dosmann | 5,745,308 A | 4/1998 | Spangenberg et al. |
| 5,489,414 A | 2/1996 | Schreiber et al. | 5,748,002 A | 5/1998 | Scott et al. |
| 5,494,638 A | 2/1996 | Gullick | 5,755,954 A | 5/1998 | Ludwig et al. |
| 5,500,350 A | 3/1996 | Baker et al. | 5,757,666 A | 5/1998 | Schreiber et al. |
| 5,502,396 A | 3/1996 | Desarzens et al. | 5,759,364 A | 6/1998 | Charlton et al. |
| 5,504,011 A | 4/1996 | Gavin et al. | 5,759,794 A | 6/1998 | Levine et al. |
| 5,508,171 A | 4/1996 | Walling et al. | 5,762,770 A | 6/1998 | Pritchard et al. |

| Patent No. | Date | Inventor(s) | Patent No. | Date | Inventor(s) |
|---|---|---|---|---|---|
| 5,776,710 A | 7/1998 | Levine et al. | 6,156,673 A | 12/2000 | Hintermaier et al. |
| 5,780,304 A | 7/1998 | Matzinger et al. | 6,159,745 A | 12/2000 | Roberts et al. |
| 5,786,584 A | 7/1998 | Button et al. | 6,162,611 A | 12/2000 | Heller et al. |
| 5,788,833 A | 8/1998 | Lewis et al. | 6,162,639 A | 12/2000 | Douglas |
| 5,789,255 A | 8/1998 | Yu | 6,168,563 B1 | 1/2001 | Brown |
| 5,792,668 A | 8/1998 | Fuller et al. | 6,168,957 B1 | 1/2001 | Matzinger et al. |
| 5,798,031 A | 8/1998 | Charlton et al. | 6,170,318 B1 | 1/2001 | Lewis |
| 5,801,057 A | 9/1998 | Smart et al. | 6,174,420 B1 | 1/2001 | Hodges et al. |
| 5,807,375 A | 9/1998 | Gross et al. | 6,175,752 B1 | 1/2001 | Say et al. |
| 5,820,551 A | 10/1998 | Hill et al. | 6,176,988 B1 | 1/2001 | Kessler |
| 5,820,662 A | 10/1998 | Kubo et al. | 6,179,979 B1 | 1/2001 | Hodges et al. |
| 5,832,921 A | 11/1998 | Lennert et al. | 6,180,062 B1 | 1/2001 | Naka et al. |
| 5,834,217 A | 11/1998 | Levine et al. | 6,193,873 B1 | 2/2001 | Oharra et al. |
| 5,837,546 A | 11/1998 | Allen et al. | 6,197,040 B1 | 3/2001 | LeVaughn et al. |
| 5,843,691 A | 12/1998 | Douglas et al. | 6,200,773 B1 | 3/2001 | Ouyang et al. |
| 5,843,692 A | 12/1998 | Phillips et al. | 6,201,607 B1 | 3/2001 | Roth et al. |
| 5,846,794 A | 12/1998 | Delobeau et al. | 6,203,952 B1 | 3/2001 | O'Brian et al. |
| 5,849,174 A | 12/1998 | Sanghera et al. | 6,206,282 B1 | 3/2001 | Hayes, Sr. et al. |
| 5,856,195 A | 1/1999 | Charlton et al. | 6,206,292 B1 | 3/2001 | Robertz et al. |
| 5,858,691 A | 1/1999 | Hoenes et al. | 6,207,000 B1 | 3/2001 | Schwobel et al. |
| 5,863,400 A | 1/1999 | Drummond et al. | 6,212,417 B1 | 4/2001 | Ikeda et al. |
| 5,865,972 A | 2/1999 | Buffle et al. | 6,218,571 B1 | 4/2001 | Zheng et al. |
| 5,873,990 A | 2/1999 | Wojciechowski et al. | 6,225,078 B1 | 5/2001 | Ikeda et al. |
| 5,874,046 A | 2/1999 | Megerle | 6,226,081 B1 | 5/2001 | Fantone et al. |
| 5,883,378 A | 3/1999 | Irish et al. | 6,233,471 B1 | 5/2001 | Berner et al. |
| 5,885,839 A | 3/1999 | Lingane et al. | 6,241,862 B1 | 6/2001 | McAleer et al. |
| 5,890,489 A | 4/1999 | Elden | 6,246,862 B1 | 6/2001 | Grivas et al. |
| 5,904,898 A | 5/1999 | Markart | 6,246,966 B1 | 6/2001 | Perry |
| 5,911,872 A | 6/1999 | Lewis et al. | 6,251,260 B1 | 6/2001 | Heller et al. |
| 5,916,156 A | 6/1999 | Hildenbrand et al. | 6,259,937 B1 | 7/2001 | Schulman et al. |
| 5,921,925 A | 7/1999 | Cartmell et al. | 6,261,519 B1 | 7/2001 | Harding et al. |
| 5,922,530 A | 7/1999 | Yu | 6,262,749 B1 | 7/2001 | Finger et al. |
| 5,922,591 A | 7/1999 | Anderson et al. | 6,268,162 B1 | 7/2001 | Phillips et al. |
| 5,925,021 A | 7/1999 | Castellano et al. | 6,270,637 B1 | 8/2001 | Crismore et al. |
| RE36,268 E | 8/1999 | Szuminsky et al. | 6,271,044 B1 | 8/2001 | Ballerstadt et al. |
| 5,942,102 A | 8/1999 | Hodges et al. | 6,272,364 B1 | 8/2001 | Kurnik |
| 5,945,341 A | 8/1999 | Howard, III | 6,275,717 B1 | 8/2001 | Gross et al. |
| 5,948,289 A | 9/1999 | Noda et al. | 6,277,641 B1 | 8/2001 | Yager |
| 5,958,199 A | 9/1999 | Miyamoto et al. | 6,281,006 B1 | 8/2001 | Heller et al. |
| 5,965,380 A | 10/1999 | Heller et al. | 6,284,125 B1 | 9/2001 | Hodges et al. |
| 5,968,760 A | 10/1999 | Phillips et al. | 6,284,550 B1 | 9/2001 | Carroll et al. |
| 5,971,923 A | 10/1999 | Finger | 6,287,595 B1 | 9/2001 | Loewy et al. |
| 5,989,917 A | 11/1999 | McAleer et al. | 6,294,281 B1 | 9/2001 | Heller |
| 6,001,239 A | 12/1999 | Douglas et al. | 6,294,787 B1 | 9/2001 | Jahne et al. |
| 6,004,441 A | 12/1999 | Fujiwara et al. | 6,295,506 B1 | 9/2001 | Heinonen et al. |
| 6,004,442 A | 12/1999 | Choulga et al. | 6,299,757 B1 | 10/2001 | Feldmen et al. |
| 6,013,170 A | 1/2000 | Meade | 6,300,123 B1 | 10/2001 | Vadgama et al. |
| 6,042,714 A | 3/2000 | Lin et al. | 6,300,961 B1 | 10/2001 | Finger et al. |
| 6,044,285 A | 3/2000 | Chaiken et al. | 6,309,526 B1 | 10/2001 | Fujiwara et al. |
| 6,045,567 A | 4/2000 | Taylor et al. | 6,315,951 B1 | 11/2001 | Markart |
| 6,054,039 A | 4/2000 | Shieh | 6,316,264 B1 | 11/2001 | Corey et al. |
| 6,061,128 A | 5/2000 | Zweig et al. | 6,326,160 B1 | 12/2001 | Dunn et al. |
| 6,069,011 A | 5/2000 | Riedel | 6,329,161 B1 | 12/2001 | Heller et al. |
| 6,071,391 A | 6/2000 | Gotoh et al. | 6,330,464 B1 | 12/2001 | Colvin, Jr. et al. |
| 6,086,748 A * | 7/2000 | Durst et al. ............... 205/775 | 6,335,203 B1 | 1/2002 | Patel et al. |
| 6,087,182 A | 7/2000 | Jeng et al. | 6,338,790 B1 | 1/2002 | Feldmen et al. |
| 6,090,268 A | 7/2000 | Akita et al. | 6,340,428 B1 | 1/2002 | Ikeada et al. |
| 6,091,975 A | 7/2000 | Daddona et al. | 6,342,364 B1 | 1/2002 | Watanabe et al. |
| 6,102,872 A | 8/2000 | Doneen et al. | 6,344,133 B1 | 2/2002 | Formica et al. |
| 6,103,033 A | 8/2000 | Say et al. | 6,349,230 B1 | 2/2002 | Kawanaka et al. |
| 6,103,509 A | 8/2000 | Sode | 6,358,752 B1 | 3/2002 | Durst et al. |
| 6,110,354 A | 8/2000 | Darling et al. | 6,377,896 B1 | 4/2002 | Sato et al. |
| 6,120,676 A | 9/2000 | Heller et al. | 6,379,513 B1 | 4/2002 | Chambers et al. |
| 6,121,009 A | 9/2000 | Heller et al. | 6,339,258 B1 | 5/2002 | O'Brien et al. |
| 6,121,050 A | 9/2000 | Han | 6,389,891 B1 | 5/2002 | D'Angelico et al. |
| 6,126,609 A | 10/2000 | Keith et al. | 6,391,558 B1 | 5/2002 | Henkens et al. |
| 6,128,519 A | 10/2000 | Say | 6,391,645 B1 | 5/2002 | Huang et al. |
| 6,129,823 A | 10/2000 | Hughes et al. | 6,394,952 B1 | 5/2002 | Anderson et al. |
| 6,134,461 A | 10/2000 | Say et al. | 6,395,227 B1 | 5/2002 | Kiser et al. |
| 6,136,549 A | 10/2000 | Feistel | 6,401,532 B2 | 6/2002 | Lubbers |
| 6,136,610 A | 10/2000 | Polito et al. | 6,413,411 B1 | 7/2002 | Pottgen et al. |
| 6,143,164 A | 11/2000 | Heller et al. | 6,414,213 B2 | 7/2002 | Ohmori et al. |
| 6,143,247 A | 11/2000 | Sheppard, Jr. et al. | 6,414,395 B1 | 7/2002 | Ookuma et al. |
| 6,144,869 A | 11/2000 | Berner et al. | 6,414,410 B1 | 7/2002 | Nakamura et al. |
| 6,150,124 A | 11/2000 | Riedel | 6,420,128 B1 | 7/2002 | Ouyang et al. |
| 6,153,069 A | 11/2000 | Pottgen et al. | 6,444,115 B1 | 9/2002 | Hodges et al. |
| RE36,991 E | 12/2000 | Yamamoto et al. | 6,447,657 B1 | 9/2002 | Bhullar et al. |
| 6,156,051 A | 12/2000 | Schraga | 6,454,921 B1 | 9/2002 | Hodges et al. |
| 6,156,173 A | 12/2000 | Gotoh et al. | 6,461,496 B1 | 10/2002 | Feldmen et al. |

| | | | | | | |
|---|---|---|---|---|---|---|
| 6,475,372 B1 | 11/2002 | Ohara et al. | | 7,351,323 B2 | 4/2008 | Iketaki et al. |
| 6,484,046 B1 | 11/2002 | Say et al. | | 7,537,684 B2 | 5/2009 | Sato et al. |
| 6,485,923 B1 | 11/2002 | Yani et al. | | 2001/0017269 A1 | 8/2001 | Heller et al. |
| 6,488,827 B1 | 12/2002 | Shartle | | 2002/0004106 A1 | 1/2002 | Leddy et al. |
| 6,489,133 B2 | 12/2002 | Phillips et al. | | 2002/0012821 A1 | 1/2002 | Leddy et al. |
| 6,491,803 B1 | 12/2002 | Shen et al. | | 2002/0053523 A1 | 5/2002 | Liamos et al. |
| 6,491,870 B2 | 12/2002 | Patel et al. | | 2002/0079219 A1 | 6/2002 | Zhao et al. |
| 6,501,976 B1 | 12/2002 | Sohrab | | 2002/0081588 A1 | 6/2002 | De Lumley-woodyear et al. |
| 6,503,381 B1 | 1/2003 | Gotoh et al. | | 2002/0084196 A1 | 7/2002 | Liamos et al. |
| 6,512,986 B1 | 1/2003 | Harmon | | 2002/0125146 A1 | 9/2002 | Chan et al. |
| 6,514,718 B2 | 2/2003 | Heller et al. | | 2002/0157967 A1 | 10/2002 | Ling et al. |
| 6,521,110 B1 | 2/2003 | Hodges et al. | | 2002/0180446 A1 | 12/2002 | Kuhr et al. |
| 6,521,182 B1 | 2/2003 | Shartle et al. | | 2003/0064525 A1 | 4/2003 | Liess |
| 6,525,330 B2 | 2/2003 | Paolini et al. | | 2003/0113933 A1 | 6/2003 | Jansson et al. |
| 6,525,549 B1 | 2/2003 | Poellmann | | 2003/0119208 A1 | 6/2003 | Jun et al. |
| 6,526,298 B1 | 2/2003 | Khalil et al. | | 2003/0136673 A1 | 7/2003 | Farruggia et al. |
| 6,531,040 B2 | 3/2003 | Musho et al. | | 2003/0148169 A1 | 8/2003 | Willmer et al. |
| 6,531,239 B2 | 3/2003 | Heller | | 2003/0159927 A1 | 8/2003 | Lewis et al. |
| 6,531,322 B1 | 3/2003 | Jurik et al. | | 2003/0175737 A1 | 9/2003 | Schulein et al. |
| 6,537,498 B1 | 3/2003 | Briglin et al. | | 2003/0176183 A1 | 9/2003 | Drucker et al. |
| 6,538,735 B1 | 3/2003 | Duebendorfer et al. | | 2003/0178322 A1 | 9/2003 | Bolon et al. |
| 6,540,890 B1 | 4/2003 | Bhullar et al. | | 2003/0201194 A1 | 10/2003 | Heller et al. |
| 6,540,891 B1 | 4/2003 | Stewart et al. | | 2003/0205465 A1 | 11/2003 | Feng et al. |
| 6,541,266 B2 | 4/2003 | Modzelewski et al. | | 2003/0209450 A1 | 11/2003 | McVey et al. |
| 6,544,474 B2 | 4/2003 | Douglas et al. | | 2004/0005716 A9 | 1/2004 | Beaty et al. |
| 6,549,796 B2 | 4/2003 | Sohrab | | 2004/0026253 A1 | 2/2004 | Leddy et al. |
| 6,551,494 B1 | 4/2003 | Heller et al. | | 2004/0033165 A1 | 2/2004 | Lewis et al. |
| 6,555,061 B1 | 4/2003 | Leong et al. | | 2004/0040840 A1 | 3/2004 | Mao et al. |
| 6,558,528 B1 | 5/2003 | Matzinger | | 2004/0054267 A1 | 3/2004 | Feldmen et al. |
| 6,558,529 B1 | 5/2003 | McVey et al. | | 2004/0055898 A1 | 3/2004 | Heller et al. |
| 6,560,471 B1 | 5/2003 | Heller et al. | | 2004/0060818 A1 | 4/2004 | Feldman et al. |
| 6,562,625 B2 | 5/2003 | Modzelewski et al. | | 2004/0072158 A1 | 4/2004 | Henkens et al. |
| 6,565,509 B1 | 5/2003 | Say et al. | | 2004/0074772 A1 | 4/2004 | Kumar et al. |
| 6,570,390 B2 | 5/2003 | Hirayama et al. | | 2004/0079653 A1 | 4/2004 | Karinka et al. |
| 6,571,651 B1 | 6/2003 | Hodges | | 2004/0099531 A1 | 5/2004 | Srinivasan et al. |
| 6,572,822 B2 | 6/2003 | Jurik et al. | | 2004/0118682 A1 | 6/2004 | Murray et al. |
| 6,574,425 B1 | 6/2003 | Weiss et al. | | 2004/0149577 A1 | 8/2004 | Kumar et al. |
| 6,576,101 B1 | 6/2003 | Heller et al. | | 2004/0157337 A1 | 8/2004 | Burke et al. |
| 6,576,117 B1 | 6/2003 | Iketaki et al. | | 2004/0157338 A1 | 8/2004 | Burke et al. |
| 6,576,416 B2 | 6/2003 | Haviland et al. | | 2004/0157339 A1 | 8/2004 | Burke et al. |
| 6,576,461 B2 | 6/2003 | Heller et al. | | 2004/0224137 A1 | 11/2004 | Rogalska et al. |
| 6,579,690 B1 | 6/2003 | Bonnecaze | | 2004/0225230 A1 | 11/2004 | Liamos et al. |
| 6,591,125 B1 | 7/2003 | Buse et al. | | 2004/0256248 A1 | 12/2004 | Burke et al. |
| 6,592,744 B1 | 7/2003 | Hodges et al. | | 2004/0259180 A1 | 12/2004 | Burke et al. |
| 6,592,745 B1 | 7/2003 | Feldmen et al. | | 2004/0260511 A1 | 12/2004 | Burke et al. |
| 6,594,514 B2 | 7/2003 | Berner et al. | | 2005/0009126 A1 | 1/2005 | Andrews et al. |
| 6,600,997 B2 | 7/2003 | Deweese et al. | | 2005/0069892 A1 | 3/2005 | Iyengar et al. |
| 6,605,200 B1 | 8/2003 | Mao et al. | | 2005/0106937 A1 | 5/2005 | Lin et al. |
| 6,605,201 B1 | 8/2003 | Mao et al. | | 2005/0164322 A1 | 7/2005 | Heller et al. |
| 6,607,658 B1 | 8/2003 | Heller et al. | | 2005/0176153 A1 | 8/2005 | O'hara et al. |
| 6,616,819 B1 | 9/2003 | Liamos et al. | | 2007/0246357 A1 | 10/2007 | Wu |
| 6,618,934 B1 | 9/2003 | Feldmen et al. | | | | |
| 6,623,501 B2 | 9/2003 | Heller et al. | | FOREIGN PATENT DOCUMENTS | | |
| 6,627,057 B1 | 9/2003 | Bhullar et al. | | | | |
| 6,632,349 B1 | 10/2003 | Hodges et al. | | CN | 1322299 | 10/2000 |
| 6,638,415 B1 | 10/2003 | Hodges et al. | | CN | 20011328156 | 12/2001 |
| 6,638,716 B2 | 10/2003 | Heller et al. | | CN | 1598564 | 10/2004 |
| 6,645,359 B1 | 11/2003 | Bhullar et al. | | DE | 229500 | 6/1985 |
| 6,645,368 B1 | 11/2003 | Beaty et al. | | DE | 1989271179 | 8/1989 |
| 6,654,625 B1 | 11/2003 | Say et al. | | DE | 19914003194 | 8/1991 |
| 6,656,702 B1 | 12/2003 | Yugawa et al. | | DE | 4100727 | 7/1992 |
| 6,676,816 B2 | 1/2004 | Mao et al. | | DE | 4318891 | 12/1994 |
| 6,676,995 B2 | 1/2004 | Dick et al. | | DE | 19824629 | 12/1999 |
| 6,689,265 B2 | 2/2004 | Chen et al. | | DE | 69915850 | 1/2005 |
| 6,689,411 B2 | 2/2004 | Dick et al. | | EP | 034049 | 8/1981 |
| 6,699,384 B1 | 3/2004 | Bennett et al. | | EP | 0057110 | 8/1982 |
| 6,749,740 B2 | 6/2004 | Liamos et al. | | EP | 0120715 | 10/1984 |
| 6,790,341 B1 | 9/2004 | Darling et al. | | EP | 0121385 | 10/1984 |
| 6,824,669 B1 | 11/2004 | Choong et al. | | EP | 0127958 | 12/1984 |
| 6,824,670 B2 | 11/2004 | Tokunaga et al. | | EP | 0132790 A2 | 2/1985 |
| 6,841,052 B2 | 1/2005 | Musho et al. | | EP | 010375 | 12/1985 |
| 6,890,421 B2 | 5/2005 | Ohara et al. | | EP | 0164180 | 12/1985 |
| 6,893,545 B2 | 5/2005 | Gotoh et al. | | EP | 0255291 | 2/1986 |
| 6,942,518 B2 | 9/2005 | Liamos et al. | | EP | 0206218 | 12/1986 |
| 7,018,843 B2 | 3/2006 | Heller | | EP | 0213343 | 3/1987 |
| 7,122,111 B2 | 10/2006 | Tokunaga et al. | | EP | 1987215678 | 3/1987 |
| 7,132,041 B2 | 11/2006 | Deng et al. | | EP | 0230472 | 8/1987 |
| 7,276,146 B2 | 10/2007 | Wilsey | | EP | 0241309 | 10/1987 |
| 7,276,147 B2 | 10/2007 | Wilsey | | EP | 0244326 | 11/1987 |
| | | | | EP | 0287883 | 10/1988 |

| | | |
|---|---|---|
| EP | 0330517 | 2/1989 |
| EP | 0354441 | 2/1990 |
| EP | 0359531 | 3/1990 |
| EP | 0359831 | 3/1990 |
| EP | 0383322 | 8/1990 |
| EP | 0417796 | 3/1991 |
| EP | 0470649 | 2/1992 |
| EP | 0471986 | 2/1992 |
| EP | 0537761 | 4/1993 |
| EP | 0546536 | 6/1993 |
| EP | 0546796 | 6/1993 |
| EP | 0628810 | 12/1994 |
| EP | 0636880 | 2/1995 |
| EP | 0640832 | 3/1995 |
| EP | 0651250 | 5/1995 |
| EP | 0186286 | 7/1996 |
| EP | 0732406 | 9/1996 |
| EP | 0732590 | 9/1996 |
| EP | 0741186 | 11/1996 |
| EP | 0800086 | 10/1997 |
| EP | 0837320 | 4/1998 |
| EP | 0840122 | 5/1998 |
| EP | 0851224 | 7/1998 |
| EP | 0859230 | 8/1998 |
| EP | 0958495 | 8/1998 |
| EP | 0878708 | 11/1998 |
| EP | 0878713 | 11/1998 |
| EP | 0887421 | 12/1998 |
| EP | 0894509 | 2/1999 |
| EP | 1042667 | 7/1999 |
| EP | 0942278 | 9/1999 |
| EP | 0964059 | 12/1999 |
| EP | 1119637 | 8/2001 |
| EP | 20031279742 | 1/2003 |
| EP | 1411348 | 4/2004 |
| ES | 2184236 | 1/2003 |
| ES | 2223185 | 2/2005 |
| FR | 2325920 | 9/1976 |
| GB | 2295676 | 6/1996 |
| JP | 198762209350 | 9/1987 |
| JP | 3260739 | 11/1991 |
| JP | 199709089832 | 4/1997 |
| JP | 11087213 | 3/1999 |
| JP | 199902120657 | 5/1999 |
| JP | 2000180399 | 6/2000 |
| JP | 2003028826 | 1/2003 |
| JP | 2003061650 | 3/2003 |
| JP | 200403478 | 1/2004 |
| JP | 2004093478 | 3/2004 |
| JP | 2004300328 | 10/2004 |
| JP | 2005147990 | 6/2005 |
| WO | WO 8101794 | 7/1981 |
| WO | WO 8203729 | 10/1982 |
| WO | WO 8300926 | 3/1983 |
| WO | WO 8600138 | 1/1986 |
| WO | WO 8602732 | 5/1986 |
| WO | WO 9005293 | 5/1990 |
| WO | WO 9005910 | 5/1990 |
| WO | WO 9109139 | 6/1991 |
| WO | WO 9201928 | 2/1992 |
| WO | WO 9207655 | 5/1992 |
| WO | WO 9215704 | 9/1992 |
| WO | WO 9215859 | 9/1992 |
| WO | WO 9215861 | 9/1992 |
| WO | WO 9215950 | 9/1992 |
| WO | WO 9219961 | 11/1992 |
| WO | WO 9222669 | 12/1992 |
| WO | WO 9309433 | 5/1993 |
| WO | WO 9321518 | 10/1993 |
| WO | WO 9325898 | 12/1993 |
| WO | WO 9403542 | 2/1994 |
| WO | WO 9412950 | 6/1994 |
| WO | WO 9416095 | 7/1994 |
| WO | WO 9423295 | 10/1994 |
| WO | WO 9428414 | 12/1994 |
| WO | WO 9429705 | 12/1994 |
| WO | WO 9503542 | 2/1995 |
| WO | WO 9507050 | 3/1995 |
| WO | WO 9522597 | 8/1995 |
| WO | WO 9528634 | 10/1995 |
| WO | WO 9604398 | 2/1996 |
| WO | WO 9607908 | 3/1996 |
| WO | WO 9613707 | 5/1996 |
| WO | WO 9614026 | 5/1996 |
| WO | WO 9615454 | 5/1996 |
| WO | WO 9633403 | 10/1996 |
| WO | WO 9700441 | 1/1997 |
| WO | WO 9702487 | 1/1997 |
| WO | WO 9708544 | 3/1997 |
| WO | WO 9716726 | 5/1997 |
| WO | WO 9718465 | 5/1997 |
| WO | WO 9729366 | 8/1997 |
| WO | WO 9729847 | 8/1997 |
| WO | WO 9730344 | 8/1997 |
| WO | WO 9739343 | 10/1997 |
| WO | WO 9742882 | 11/1997 |
| WO | WO 9742888 | 11/1997 |
| WO | WO 9745719 | 12/1997 |
| WO | WO 9805424 | 2/1998 |
| WO | WO 9819153 | 5/1998 |
| WO | WO 9819159 | 5/1998 |
| WO | WO 9829740 | 7/1998 |
| WO | WO 9835225 | 8/1998 |
| WO | WO 98/44342 | 10/1998 |
| WO | WO 98/58246 | 12/1998 |
| WO | WO 98/58250 | 12/1998 |
| WO | WO 9857159 | 12/1998 |
| WO | WO 9922227 | 5/1999 |
| WO | WO 9922230 | 5/1999 |
| WO | 9938003 | 7/1999 |
| WO | WO 9932881 | 7/1999 |
| WO | WO 9945375 | 9/1999 |
| WO | WO 9967628 | 12/1999 |
| WO | WO 0016089 | 3/2000 |
| WO | WO 0020626 | 4/2000 |
| WO | WO 0020855 | 4/2000 |
| WO | WO 0029540 | 5/2000 |
| WO | WO 0057011 | 9/2000 |
| WO | WO 0077523 | 12/2000 |
| WO | WO 0103207 | 1/2001 |
| WO | WO 0121827 | 3/2001 |
| WO | WO 0133206 | 5/2001 |
| WO | WO 0133216 | 5/2001 |
| WO | WO 0156771 | 8/2001 |
| WO | WO 0157510 | 8/2001 |
| WO | WO 0157513 | 8/2001 |
| WO | WO 0165246 | 9/2001 |
| WO | WO 0167099 | 9/2001 |
| WO | WO 0201214 | 1/2002 |
| WO | WO 0231481 | 4/2002 |
| WO | WO 0231482 | 4/2002 |
| WO | WO 02077633 | 10/2002 |
| WO | WO 03001195 | 1/2003 |
| WO | WO 03069304 | 2/2003 |
| WO | WO 03066554 | 6/2003 |
| WO | WO 03087802 | 10/2003 |
| WO | WO 2004023128 | 3/2004 |
| WO | WO 2004046707 | 6/2004 |
| WO | WO 2004053476 | 6/2004 |
| WO | WO 2004062801 | 7/2004 |
| WO | WO 2004113896 | 12/2004 |
| WO | WO 2004113912 | 12/2004 |
| WO | WO 2004113913 | 12/2004 |
| WO | WO 2005001462 | 1/2005 |
| WO | WO 2005001463 | 1/2005 |
| WO | WO 2005003748 | 1/2005 |
| WO | WO 2005008231 | 1/2005 |
| WO | WO 2005022143 | 3/2005 |
| WO | WO 2006042304 | 4/2006 |
| WO | WO 2006079797 | 8/2006 |

OTHER PUBLICATIONS

WIPO, "Search Report and Written Opinion for SG 200800290-9", Feb. 10, 2009, Publisher: Intellectual Property Office of Singapore, Published in: Singapore.
Patent Office of The Russian Federation, "Official Action", Jun. 3, 2010, Published in: Russian Federation.

EPO, "Search Report and Written Opionion for PCT/US2006/028013", Dec. 6, 2006, Publisher: International Searching Authority.

Yao, et al., "The Low-Potenetail Approach of Glucose Sensing", 1986, pp. 139-146, vol. BME-33, No. 2.

Dalrymple, et al., "Peak Shapes in Semidifferential Electroanalysis", Aug. 9, 1977, pp. 1390-1394, vol. 49, No. 9.

Yao, et al, "A Thin-Film Glucose Electrode System with Compensation for Drifit", 1989, pp. 742-744, vol. XXXV.

Gunasingham, et al., "Pulsed amperometric detection of glucose using a mediated enzyme electrode", "Journal of Electroanalytical Chemisty", 1990, pp. 349-362, vol. 287, No. 2.

* cited by examiner

GATED AMPEROMETRY

REFERENCE TO RELATED APPLICATIONS

This application is a continuation of PCT/US2006/028013 entitled "Gated Amperometry" filed Jul. 19, 2006, which was published in English and claimed the benefit of U.S. Provisional Application No. 60/700,787 entitled "Gated Amperometry" as filed on Jul. 20, 2005, and U.S. Provisional Application No. 60/746,771 entitled "Abnormal Output Detection System for a Biosensor" as filed on May 8, 2006, each of which are incorporated herein by reference.

BACKGROUND

The quantitative determination of analytes in biological fluids is useful in the diagnosis and treatment of physiological abnormalities. For example, determining the glucose level in biological fluids, such as blood, is important to diabetic individuals who must frequently check their blood glucose level to regulate their diets and/or medication.

Electrochemical systems have been used for this type of analysis. During the analysis, the analyte undergoes a redox reaction with an enzyme or similar species to generate an electric current that may be measured and correlated with the concentration of the analyte. A substantial benefit may be provided to the user by decreasing the time required for the analysis while supplying the desired accuracy and precision.

One example of an electrochemical sensor system for analyzing analytes in biological fluids includes a measuring device and a sensor strip. The sensor strip includes reagents to react with and transfer electrons from the analyte during the analysis and electrodes to pass the electrons through conductors that connect the strip with the device. The measuring device includes contacts to receive the electrons from the strip and the ability to apply a voltage differential between the contacts. The device may record the current passing through the sensor and translate the current values into a measure of the analyte content of the sample. These sensor systems may analyze a single drop of whole blood (WB), such as from 1-15 microliters (µL) in volume.

Examples of bench-top measuring devices include the BAS 100B Analyzer available from BAS Instruments in West Lafayette, Ind.; the CH Instrument Analyzer available from CH Instruments in Austin, Tex.; the Cypress Electrochemical Workstation available from Cypress Systems in Lawrence, Kans.; and the EG&G Electrochemical Instrument available from Princeton Research Instruments in Princeton, N.J. Examples of portable measuring devices include the Ascensia Breeze® and Elite® meters of Bayer Corporation.

The sensor strip may include a working electrode where the analyte undergoes electrochemical reaction and a counter electrode where the opposite electrochemical reaction occurs, thus allowing current to flow between the electrodes. Thus, if oxidation occurs at the working electrode, reduction occurs at the counter electrode. See, for example, *Fundamentals Of Analytical Chemistry*, 4th Edition, D. A. Skoog and D. M. West; Philadelphia: Saunders College Publishing (1982), pp 304-341.

The sensor strip also may include a true reference electrode to provide a non-variant reference potential to the measuring device. While multiple reference electrode materials are known, a mixture of silver (Ag) and silver chloride (AgCl) is typical due to the insolubility of the mixture in the aqueous environment of the analysis solution. A reference electrode also may be used as the counter electrode. A sensor strip using such a combination reference-counter electrode is described in U.S. Pat. No. 5,820,551.

The sensor strip may be formed by printing electrodes on an insulating substrate using multiple techniques, such as those described in U.S. Pat. Nos. 6,531,040; 5,798,031; and 5,120,420. One or more reagent layer may be formed by coating one or more of the electrodes, such as the working and/or counter electrodes. In one aspect, more than one of the electrodes may be covered by the same reagent layer, such as when the working and counter electrodes are coated by the same composition. In another aspect, reagent layers having different compositions may be printed or micro-deposited onto the working and counter electrodes using the method described in a U.S. provisional patent application filed Oct. 24, 2003, Application No. 60/513,817. Thus, the reagent layer on the working electrode may contain the enzyme, the mediator, and a binder while the reagent layer on the counter electrode contains a soluble redox species, which could be the same as the mediator or different, and a binder.

The reagent layer may include an ionizing agent for facilitating the oxidation or reduction of the analyte, as well as any mediators or other substances that assist in transferring electrons between the analyte and the conductor. The ionizing agent may be an analyte specific enzyme, such as glucose oxidase or glucose dehydrogenase, to catalyze the oxidation of glucose in a whole blood (WB) sample. The reagent layer also may include a binder that holds the enzyme and mediator together. Table I, below, provides conventional combinations of enzymes and mediators for use with specific analytes.

TABLE I

| Analyte | Enzyme | Mediator |
| --- | --- | --- |
| Glucose | Glucose Oxidase | Ferricyanide |
| Glucose | Glucose Dehydrogenase | Ferricyanide |
| Cholesterol | Cholesterol Oxidase | Ferricyanide |
| Lactate | Lactate Oxidase | Ferricyanide |
| Uric Acid | Uricase | Ferricyanide |
| Alcohol | Alcohol Oxidase | Phenylenediamine |

The binder may include various types and molecular weights of polymers, such as CMC (carboxyl methyl cellulose) and/or PEO (polyethylene oxide). In addition to binding the reagents together, the binder may assist in filtering red blood cells, preventing them from coating the electrode surface.

Examples of conventional electrochemical sensor systems for analyzing analytes in biological fluids include the Precision® biosensors available from Abbott in Abbott Park, Ill.; Accucheck® biosensors available from Roche in Indianapolis, Ind.; and OneTouch Ultra® biosensors available from Lifescan in Milpitas, Calif.

One electrochemical method, which has been used to quantify analytes in biological fluids, is coulometry. For example, Heller et al. described the coulometric method for whole blood glucose measurements in U.S. Pat. No. 6,120,676. In coulometry, the analyte concentration is quantified by exhaustively oxidizing the analyte within a small volume and integrating the current over the time of oxidation to produce the electrical charge representing the analyte concentration. In other words, coulometry captures the total amount of glucose within the sensor strip.

An important aspect of coulometry is that towards the end of the integration curve of charge vs. time, the rate at which the current changes with time becomes substantially constant to yield a steady-state condition. This steady-state portion of the coulometric curve forms a relatively flat plateau region, thus allowing determination of the corresponding current. However, the coulometric method requires the complete conversion of the entire volume of analyte to reach the steady-state condition. As a result, this method is time consuming and does not provide the fast results which users of electrochemical devices, such as glucose-monitoring products, demand. Another problem with coulometry is that the small volume of the sensor cell must be controlled in order to provide accurate results, which can be difficult with a mass produced device.

Another electrochemical method which has been used to quantify analytes in biological fluids is amperometry. In amperometry, current is measured during a read pulse as a constant potential (voltage) is applied across the working and counter electrodes of the sensor strip. The measured current is used to quantify the analyte in the sample. Amperometry measures the rate at which the electrochemically active species, and thus the analyte, is being oxidized or reduced near the working electrode. Many variations of the amperometric method for biosensors have been described, for example in U.S. Pat. Nos. 5,620,579; 5,653,863; 6,153,069; and 6,413,411.

A disadvantage of conventional amperometric methods is the non-steady-state nature of the current after a potential is applied. The rate of current change with respect to time is very fast initially and becomes slower as the analysis proceeds due to the changing nature of the underlying diffusion process. Until the consumption rate of the reduced mediator at the electrode surface equals the diffusion rate, a steady-state current cannot be obtained. Thus, for amperometry methods, measuring the current during the transient period before a steady-state condition is reached may be associated with more inaccuracy than a measurement taken during a steady-state time period.

The "hematocrit effect" provides an impediment to accurately analyzing the concentration of glucose in WB samples. WB samples contain red blood (RB) cells and plasma. The plasma is mostly water, but contains some proteins and glucose. Hematocrit is the volume of the RB cell constituent in relation to the total volume of the WB sample and is often expressed as a percentage. Whole blood samples generally have hematocrit percentages ranging from 20% to 60%, with ~40% being the average.

In conventional sensor strips for determining glucose concentrations, glucose may be oxidized by an enzyme, which then transfers the electron to a mediator. This reduced mediator then travels to the working electrode where it is electrochemically oxidized. The amount of mediator being oxidized may be correlated to the current flowing between the working and counter electrodes of the sensor strip. Quantitatively, the current measured at the working electrode is directly proportional to the diffusion coefficient of the mediator. The hematocrit effect interferes with this process because the RB cells block the diffusion of the mediator to the working electrode. Subsequently, the hematocrit effect influences the amount of current measured at the working electrode without any connection to the amount of glucose in the sample.

WB samples having varying concentrations of RB cells may cause inaccuracies in the measurement because the sensor may not distinguish between a lower mediator concentration and a higher mediator concentration where the RB cells block diffusion to the working electrode. For example, when WB samples containing identical glucose levels, but having hematocrits of 20, 40, and 60%, are analyzed, three different glucose readings will be reported by a conventional sensor system based on one set of calibration constants (slope and intercept, for instance). Even though the glucose concentrations are the same, the system will report that the 20% hematocrit sample contains more glucose than the 60% hematocrit sample due to the RB cells interfering with diffusion of the mediator to the working electrode.

The normal hematocrit range (RBC concentration) for humans is from 20% to 60% and is centered around 40%. Hematocrit bias refers to the difference between the reference glucose concentration obtained with a reference instrument, such as the YSI 2300 STAT PLUS™ available from YSI Inc., Yellow Springs, Ohio, and an experimental glucose reading obtained from a portable sensor system for samples containing differing hematocrit levels. The difference between the reference and experimental readings results from the varying hematocrit levels between specific whole blood samples.

In addition to the hematocrit effect, measurement inaccuracies also may arise when the measurable species concentration does not correlate with the analyte concentration. For example, when a sensor system determines the concentration of a reduced mediator generated in response to the oxidation of an analyte, any reduced mediator not generated by oxidation of the analyte will lead to the sensor system indicating that more analyte is present in the sample than is correct due to mediator background.

In addition to the hematocrit and mediator background effects, other factors also may lead to inaccuracies in the ability of a conventional electrochemical sensor system to determine the concentration of an analyte in a sample. In one aspect, these inaccuracies may be introduced because the portion of the sensor strip that contains the sample may vary in volume from strip to strip. Inaccuracies also may be introduced when sufficient sample is not provided to completely fill the volume of the cap-gap, a condition referred to as under-fill. In other aspects, inaccuracies may be introduced into the measurement by random "noise" and when the sensor system lacks the ability to accurately determine temperature changes in the sample.

In an attempt to overcome one or more of these disadvantages, conventional sensor systems have attempted multiple techniques, not only with regard to the mechanical design of the sensor strip and reagent selection, but also regarding the manner in which the measuring device applies the electric potential to the strip. For example, conventional methods of reducing the hematocrit effect for amperometric sensors include the use of filters, as disclosed in U.S. Pat. Nos. 5,708,247 and 5,951,836; reversing the polarity of the applied current, as disclosed in WO 01/57510; and by methods that maximize the inherent resistance of the sample, as disclosed in U.S. Pat. No. 5,628,890.

Multiple methods of applying the electric potential to the strip, commonly referred to as pulse methods, sequences, or cycles, have been used to address inaccuracies in the determined analyte concentration. For example, in U.S. Pat. No. 4,897,162 the pulse method includes a continuous application of rising and falling voltage potentials that are commingled to give a triangular-shaped wave. Furthermore, WO 2004/053476 and U.S. Publication Nos. 2003/0178322 and 2003/0113933 describe pulse methods that include the continuous application of rising and falling voltage potentials that also change polarity.

Other conventional methods combine a specific electrode configuration with a pulse sequence adapted to that configuration. For example, U.S. Pat. No. 5,942,102 combines the specific electrode configuration provided by a thin layer cell with a continuous pulse so that the reaction products from the counter electrode arrive at the working electrode. This combination is used to drive the reaction until the current change verses time becomes constant, thus reaching a true steady state condition for the mediator moving between the working and counter electrodes during the potential step. While each of these methods balances various advantages and disadvantages, none are ideal.

As may be seen from the above description, there is an ongoing need for improved electrochemical sensor systems, especially those that may provide increasingly accurate determination of the analyte concentration in less time. The systems, devices, and methods of the present invention overcome at least one of the disadvantages associated with conventional systems.

SUMMARY

A method of determining the concentration of an analyte in a sample is provided that includes applying a pulse sequence to the sample, the pulse sequence including at least 3 duty cycles within 180 seconds. The duty cycles may each include an excitation at a fixed potential, during which a current may be recorded, and a relaxation. The pulse sequence may include a terminal read pulse and may be applied to a sensor strip including a diffusion barrier layer (DBL) on a working electrode. The determined analyte concentration may include less bias attributable to mediator background than the same or another method lacking the pulse sequence including at least 3 duty cycles within 180 seconds. Through the use of transient current data, the concentration of the analyte may be determined when a steady-state condition is not reached during the excitation portions of the duty cycles of the pulse sequence. A data treatment may be applied to the measured currents to determine the concentration of the analyte in the sample.

A handheld analyte measuring device is provided for determining the concentration of an analyte in a sample. The device includes a gated amperometric measuring device adapted to receive a sensor strip. The gated amperometric measuring device includes at least two device contacts in electrical communication with a display through electrical circuitry. The sensor strip includes at least first and second sensor strip contacts. The first sensor strip contact is in electrical communication with a working electrode and the second sensor strip contact is in electrical communication with a counter electrode through conductors. A first reagent layer is on at least one of the electrodes and includes an oxidoreductase and at least one species of a redox pair.

A handheld measuring device adapted to receive a sensor strip is provided for determining the concentration of an analyte in a sample. The device includes contacts, at least one display, and electronic circuitry establishing electrical communication between the contacts and the display. The circuitry includes an electric charger and a processor, where the processor is in electrical communication with a computer readable storage medium. The medium includes computer readable software code, which when executed by the processor, causes the charger to implement a pulse sequence comprising at least 3 duty cycles within 180 seconds between the contacts.

A method of reducing the bias attributable to mediator background in a determined concentration of an analyte in a sample is provided that includes applying a pulse sequence including at least 3 duty cycles within 180 seconds to the sample.

A method of determining the duration of a pulse sequence including at least 3 duty cycles within 180 seconds, for determining the concentration of an analyte in a sample is provided that includes determining a plurality of sets of calibration constants determined from currents recorded during the at least 3 duty cycles and determining the duration of the pulse sequence in response to the determined concentration of the analyte in the sample.

A method of signaling a user to add additional sample to a sensor strip is provided that includes determining if the sensor strip is under-filled by determining a decay constant from currents recorded during a gated amperometric pulse sequence and signaling the user to add additional sample to the sensor strip if the strip is under-filled.

A method of determining the temperature of a sample contained by a sensor strip is provided that includes determining a decay constant from currents recorded during a gated amperometric pulse sequence and correlating the decay constant with a temperature value.

A method of determining the duration of a pulse sequence for determining the concentration of an analyte in a sample is provided that includes determining the temperature of a sample contained by a sensor strip from decay constants determined from currents recorded during a gated amperometric pulse sequence.

The following definitions are included to provide a clear and consistent understanding of the specification and claims.

The term "analyte" is defined as one or more substances present in a sample. The analysis determines the presence and/or concentration of the analyte present in the sample.

The term "sample" is defined as a composition that may contain an unknown amount of the analyte. Typically, a sample for electrochemical analysis is in liquid form, and preferably the sample is an aqueous mixture. A sample may be a biological sample, such as blood, urine, or saliva. A sample also may be a derivative of a biological sample, such as an extract, a dilution, a filtrate, or a reconstituted precipitate.

The term "measurable species" is defined as any electrochemically active species that may be oxidized or reduced under an appropriate potential at the working electrode of an electrochemical sensor strip. Examples of measurable species include analytes, oxidoreductases, and mediators.

The term "amperometry" is defined as an analysis method where the concentration of an analyte in a sample is determined by electrochemically measuring the oxidation or reduction rate of the analyte at a potential.

The term "system" or "sensor system" is defined as a sensor strip in electrical communication through its conductors with a measuring device, which allows for the quantification of an analyte in a sample.

The term "sensor strip" is defined as a device that contains the sample during the analysis and provides electrical communication between the sample and the measuring device. The portion of the sensor strip that contains the sample is often referred to as the "cap-gap."

The term "conductor" is defined as an electrically conductive substance that remains stationary during an electrochemical analysis.

The term "measuring device" is defined as one or more electronic devices that may apply an electric potential to the conductors of a sensor strip and measure the resulting current. The measuring device also may include the processing capability to determine the presence and/or concentration of one or more analytes in response to the recorded current values.

The term "accuracy" is defined as how close the amount of analyte measured by a sensor strip corresponds to the true amount of analyte in the sample. In one aspect, accuracy may be expressed in terms of bias.

The term "precision" is defined as how close multiple analyte measurements are for the same sample. In one aspect, precision may be expressed in terms of the spread or variance among multiple measurements.

The term "redox reaction" is defined as a chemical reaction between two species involving the transfer of at least one electron from a first species to a second species. Thus, a redox reaction includes an oxidation and a reduction. The oxidation half-cell of the reaction involves the loss of at least one electron by the first species, while the reduction half-cell involves the addition of at least one electron to the second species. The ionic charge of a species that is oxidized is made more positive by an amount equal to the number of electrons removed. Likewise, the ionic charge of a species that is reduced is made less positive by an amount equal to the number of electrons gained.

The term "mediator" is defined as a substance that may be oxidized or reduced and that may transfer one or more electrons. A mediator is a reagent in an electrochemical analysis and is not the analyte of interest, but provides for the indirect measurement of the analyte. In a simplistic system, the mediator undergoes a redox reaction in response to the oxidation or reduction of the analyte. The oxidized or reduced mediator then undergoes the opposite reaction at the working electrode of the sensor strip and is regenerated to its original oxidation number.

The term "binder" is defined as a material that provides physical support and containment to the reagents while having chemical compatibility with the reagents.

The term "mediator background" is defined as the bias introduced into the measured analyte concentration attributable to measurable species not responsive to the underlying analyte concentration.

The term "under-fill" is defined as when insufficient sample was introduced into the sensor strip to obtain an accurate analysis.

The term "redox pair" is defined as two conjugate species of a chemical substance having different oxidation numbers. Reduction of the species having the higher oxidation number produces the species having the lower oxidation number. Alternatively, oxidation of the species having the lower oxidation number produces the species having the higher oxidation number.

The term "oxidation number" is defined as the formal ionic charge of a chemical species, such as an atom. A higher oxidation number, such as (III), is more positive, and a lower oxidation number, such as (II), is less positive.

The term "soluble redox species" is defined as a substance that is capable of undergoing oxidation or reduction and that is soluble in water (pH 7, 25° C.) at a level of at least 1.0 grams per Liter. Soluble redox species include electro-active organic molecules, organotransition metal complexes, and transition metal coordination complexes. The term "soluble redox species" excludes elemental metals and lone metal ions, especially those that are insoluble or sparingly soluble in water.

The term "oxidoreductase" is defined as any enzyme that facilitates the oxidation or reduction of an analyte. An oxidoreductase is a reagent. The term oxidoreductase includes "oxidases," which facilitate oxidation reactions where molecular oxygen is the electron acceptor; "reductases," which facilitate reduction reactions where the analyte is reduced and molecular oxygen is not the analyte; and "dehydrogenases," which facilitate oxidation reactions where molecular oxygen is not the electron acceptor. See, for example, *Oxford Dictionary of Biochemistry and Molecular Biology, Revised Edition*, A. D. Smith, Ed., New York: Oxford University Press (1997) pp. 161, 476, 477, and 560.

The term "electro-active organic molecule" is defined as an organic molecule lacking a metal that is capable of undergoing an oxidation or reduction reaction. Electro-active organic molecules may serve as mediators.

The term "organotransition metal complex," also referred to as "OTM complex," is defined as a complex where a transition metal is bonded to at least one carbon atom through a sigma bond (formal charge of −1 on the carbon atom sigma bonded to the transition metal) or a pi bond (formal charge of 0 on the carbon atoms pi bonded to the transition metal). For example, ferrocene is an OTM complex with two cyclopentadienyl (Cp) rings, each bonded through its five carbon atoms to an iron center by two pi bonds and one sigma bond. Another example of an OTM complex is ferricyanide (III) and its reduced ferrocyanide (II) counterpart, where six cyano ligands (formal charge of −1 on each of the 6 ligands) are sigma bonded to an iron center through the carbon atoms.

The term "coordination complex" is defined as a complex having well-defined coordination geometry, such as octahedral or square planar. Unlike OTM complexes, which are defined by their bonding, coordination complexes are defined by their geometry. Thus, coordination complexes may be OTM complexes (such as the previously mentioned ferricyanide), or complexes where non-metal atoms other than carbon, such as heteroatoms including nitrogen, sulfur, oxygen, and phosphorous, are datively bonded to the transition metal center. For example, ruthenium hexaamine is a coordination complex having a well-defined octahedral geometry where six $NH_3$ ligands (formal charge of 0 on each of the 6 ligands) are datively bonded to the ruthenium center. A more complete discussion of organotransition metal complexes, coordination complexes, and transition metal bonding may be found in Collman et al., Principles and Applications of Organotransition Metal Chemistry (1987) and Miessler & Tarr, Inorganic Chemistry (1991).

The term "steady-state" is defined as when the change in electrochemical signal (current) with respect to its independent input variable (voltage or time) is substantially constant, such as within ±10 or ±5%.

The term "transient point" is defined as the current value obtained as a function of time when an increasing rate of diffusion of a measurable species to a conductor surface transitions into a relatively constant rate of diffusion. Before the transient point, the current is rapidly changing with time. Similarly, after the transient point, the rate of current decay becomes relatively constant, thus reflecting the relatively constant rate of diffusion of a measurable species to a conductor surface.

The term "relatively constant" is defined as when the change in a current value or a diffusion rate is within ±20, ±10, or ±5%.

The term "average initial thickness" refers to the average height of a layer prior to the introduction of a liquid sample. The term average is used because the top surface of the layer is uneven, having peaks and valleys.

The term "redox intensity" (RI) is defined as the total excitation time divided by the sum of the total excitation time and the total relaxation time delays for a pulse sequence.

The term "handheld device" is defined as a device that may be held in a human hand and is portable. An example of a handheld device is the measuring device accompanying Ascensia® Elite Blood Glucose Monitoring System, available from Bayer HealthCare, LLC, Tarrytown, N.Y.

The term "on" is defined as "above" and is relative to the orientation being described. For example, if a first element is deposited over at least a portion of a second element, the first element is said to be "deposited on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating may be described as "on" the first element. Thus, the use of the term "on" may or may not mean that the two elements being related are in physical contact.

BRIEF DESCRIPTION OF THE DRAWINGS

The invention may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

The present invention makes use of the discovery that gated amperometric pulse sequences including multiple duty cycles may provide improved accuracy and precision to an analysis, while reducing the completion time of the analysis. Each duty cycle includes an excitation that may be provided at a relatively constant voltage. Each duty cycle also includes a relaxation that may be provided by an open circuit. The pulse sequences of the present invention may reduce the time required for analysis by eliminating the need for additional delays and pulses, such as "incubation" delays to provide reagent rehydration, "burn-off" pulses to renew the electrodes, and mediator regeneration pulses to renew the oxidation state of the mediator, thus reducing analysis time.

Even with shorter analysis times, the gated amperometric pulse sequences of the present invention may improve accuracy and/or precision in relation to conventional methods. In one aspect, accuracy errors introduced by the hematocrit effect and precision errors introduced by varying cap-gap volume may be reduced through the combination of a diffusion barrier layer with the pulse sequences of the present invention. In another aspect, errors otherwise resulting from a non-steady-state sensor condition and/or mediator background may be reduced. The gated pulse sequences of the present invention also may allow the determination of transient current and contour profiles that simulate a steady-state condition. The transient current profiles may be used to provide a plurality of sets of calibration constants, under-fill detection, and the ability to determine the temperature of the sample, instead of relying on the temperature from the measuring device.

Figure 1A:
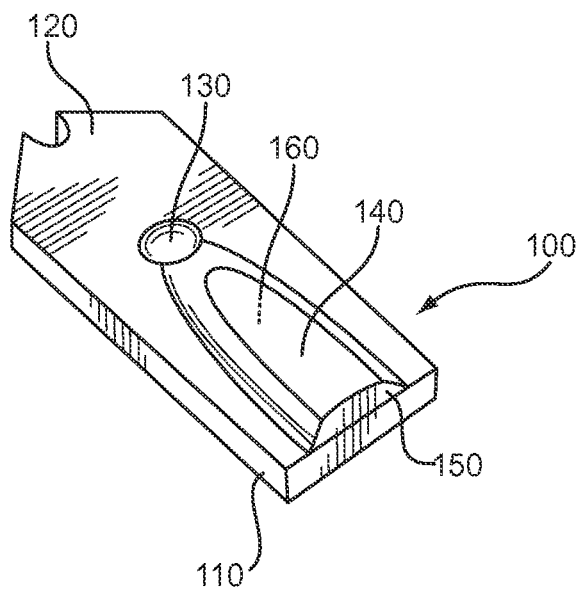
FIG. 1A is a perspective representation of an assembled sensor strip.
Figure 1B:
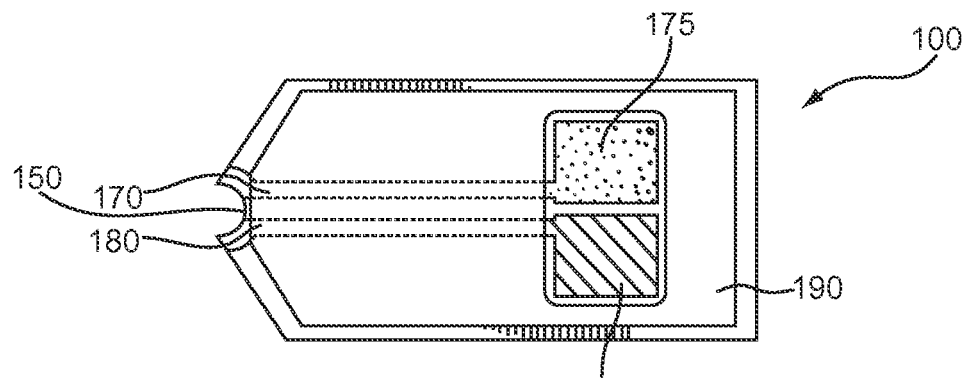
FIG. 1B is a top-view diagram of a sensor strip, with the lid removed.

FIGS. 1A and 1B depict a sensor strip 100, which may be used in the present invention. FIG. 1A is a perspective representation of an assembled sensor strip 100 including a sensor base 110, at least partially covered by a lid 120 that includes a vent 130, a concave area 140, and an input end opening 150. A partially-enclosed volume 160 (the cap-gap) is formed between the base 110 and the lid 120. Other sensor strip designs compatible with the present invention also may be used, such as those described in U.S. Pat. Nos. 5,120,420 and 5,798,031.

A liquid sample for analysis may be transferred into the cap-gap 160 by introducing the liquid to the opening 150. The liquid fills the cap-gap 160 while expelling the previously contained air through the vent 130. The cap-gap 160 may contain a composition (not shown) that assists in retaining the liquid sample in the cap-gap. Examples of such compositions include water-swellable polymers, such as carboxymethyl cellulose and polyethylene glycol; and porous polymer matrices, such as dextran and polyacrylamide.

FIG. 1B depicts a top-view of the sensor strip 100, with the lid 120 removed. Conductors 170 and 180 may run under a dielectric layer 190 from the opening 150 to a working electrode 175 and a counter electrode 185, respectively. In one aspect, the working and counter electrodes 175, 185 may be in substantially the same plane, as depicted in the figure. In a related aspect, the working and counter electrodes 175, 185 may be separated by greater than 200 or 250 μm and may be separated from an upper portion of the lid 120 by at least 100 μm. The dielectric layer 190 may partially cover the electrodes 175, 185 and may be made from any suitable dielectric material, such as an insulating polymer.

The counter electrode 185 balances the potential at the working electrode 175 of the sensor strip 100. In one aspect, this potential may be a reference potential achieved by forming the counter electrode 185 from a redox pair, such as Ag/AgCl, to provide a combined reference-counter electrode. In another aspect, the potential may be provided to the sensor system by forming the counter electrode 185 from an inert material, such as carbon, and including a soluble redox species, such as ferricyanide, within the cap-gap 160. Alternatively, the sensor strip 100 may be provided with a third conductor and electrode (not shown) to provide a reference potential to the sensor system.

Figure 2:
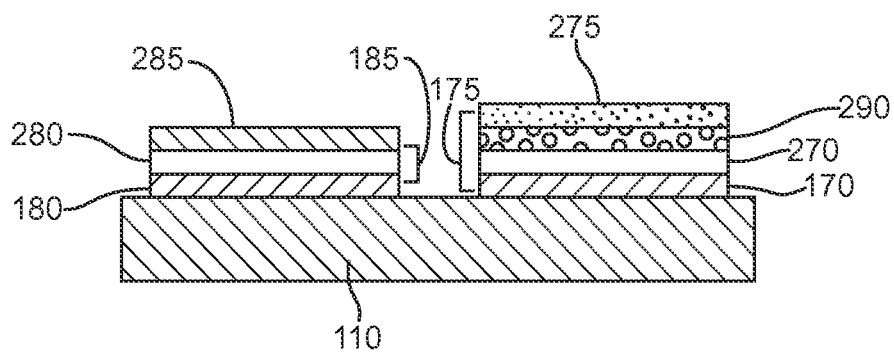
FIG. 2 depicts an end-view diagram of the sensor strip of FIG. 1B.

FIG. 2 depicts an end-view diagram of the sensor strip depicted in FIG. 1B showing the layer structure of the working electrode 175 and the counter electrode 185. The conductors 170 and 180 may lie directly on the base 110. Surface conductor layers 270 and 280 optionally may be deposited on the conductors 170 and 180, respectively. The surface conductor layers 270, 280 may be made from the same or from different materials.

The material or materials used to form the conductors 170, 180 and the surface conductor layers 270, 280 may include any electrical conductor. Preferable electrical conductors are non-ionizing, such that the material does not undergo a net oxidation or a net reduction during analysis of the sample. The conductors 170, 180 preferably include a thin layer of a metal paste or metal, such as gold, silver, platinum, palladium, copper, or tungsten. The surface conductor layers 270, 280 preferably include carbon, gold, platinum, palladium, or combinations thereof. If a surface conductor layer is not present on a conductor, the conductor is preferably made from a non-ionizing material.

The surface conductor material may be deposited on the conductors 170, 180 by any conventional means compatible with the operation of the sensor strip, including foil deposition, chemical vapor deposition, slurry deposition, and the like. In the case of slurry deposition, the mixture may be applied as an ink to the conductors 170, 180, as described in U.S. Pat. No. 5,798,031.

The reagent layers 275 and 285 may be deposited on the conductors 170 and 180, respectively, and include reagents and optionally a binder. The binder material is preferably a polymeric material that is at least partially water-soluble. Suitable partially water-soluble polymeric materials for use as the binder may include poly(ethylene oxide) (PEO), carboxy methyl cellulose (CMC), polyvinyl alcohol (PVA), hydroxyethylene cellulose (HEC), hydroxypropyl cellulose (HPC), methyl cellulose, ethyl cellulose, ethyl hydroxyethyl cellulose, carboxymethyl ethyl cellulose, polyvinyl pyrrolidone (PVP), polyamino acids such as polylysine, polystyrene sulfonate, gelatin, acrylic acid, methacrylic acid, starch, maleic anhydride salts thereof, derivatives thereof, and combinations thereof. Among the above binder materials, PEO, PVA, CMC, and PVA are preferred, with CMC and PEO being more preferred at present.

In addition to the binder, the reagent layers 275 and 285 may include the same or different reagents. In one aspect, the reagents present in the first layer 275 may be selected for use with the working electrode 175, while the reagents present in the second layer 285 may be selected for use with the counter electrode 185. For example, the reagents in the layer 285 may facilitate the free flow of electrons between the sample and the conductor 180. Similarly, the reagents in the layer 275 may facilitate the reaction of the analyte.

The reagent layer 275 may include an oxidoreductase specific to the analyte that may facilitate the reaction of the analyte while enhancing the specificity of the sensor system to the analyte, especially in complex biological samples. Examples of some specific oxidoreductases and corresponding analytes are given below in Table II.

TABLE II

| Oxidoreductase (reagent layer) | Analyte |
|---|---|
| Glucose dehydrogenase | β-glucose |
| Glucose oxidase | β-glucose |
| Cholesterol esterase; cholesterol oxidase | Cholesterol |
| Lipoprotein lipase; glycerol kinase; glycerol-3-phosphate oxidase | Triglycerides |
| Lactate oxidase; lactate dehydrogenase; diaphorase | Lactate |
| Pyruvate oxidase | Pyruvate |
| Alcohol oxidase | Alcohol |
| Bilirubin oxidase | Bilirubin |
| Uricase | Uric acid |
| Glutathione reductase | NAD(P)H |
| Carbon monoxide oxidoreductase | Carbon monoxide |

At present, especially preferred oxidoreductases for glucose analysis include glucose oxidase, glucose dehydrogenase, derivatives thereof, or combinations thereof.

The reagent layer 275 also may include a mediator to more effectively communicate the results of the analyte reaction to the surface conductor 270 and/or the conductor 170. Examples of mediators include OTM complexes, coordination complexes, and electro-active organic molecules. Specific examples include ferrocene compounds, ferrocyanide, ferricyanide, coenzymes of substituted or unsubstituted pyrroloquinoline quinones (PQQ), substituted or unsubstituted 3-phenylimino-3H-phenothiazines (PIPT), 3-phenylimino-3H-phenoxazine (PIPO), substituted or unsubstituted benzoquinones, substituted or unsubstituted naphthoquinones, N oxides, nitroso compounds, hydroxylamines, oxines, flavins, phenazines, phenazine derivatives, phenothiazines, indophenols, and indamines. These, and other mediators that may be included in the reagent layer may be found in U.S. Pat. Nos. 5,653,863; 5,520,786; 4,746,607; 3,791,988; and in EP Patent Nos. 0354441 and 0330517.

At present, especially preferred mediators for glucose analysis include ferricyanide, ruthenium hexaamine, PIPT, PIPO, or combinations thereof. A review of useful electrochemical mediators for biological redox systems may be found in *Analytica Clinica Acta*, 140 (1982), pages 1-18.

The reagent layers 275, 285 may be deposited by any convenient means, such as printing, liquid deposition, or ink-jet deposition. In one aspect, the layers are deposited by printing. With other factors being equal, the angle of the printing blade may inversely affect the thickness of the reagent layers. For example, when the blade is moved at an approximately 82° angle to the base 110, the layer may have a thickness of approximately 10 μm. Similarly, when a blade angle of approximately 62° to the base 110 is used, a thicker 30 μm layer may be produced. Thus, lower blade angles may provide thicker reagent layers. In addition to blade angle, other factors, such as the viscosity of the material being applied as well as the screen-size and emulsion combination, may affect the resulting thickness of the reagent layers 275, 285.

The working electrode 175 also may include a diffusion barrier layer (DBL) that is integral to a reagent layer 275 or that is a distinct layer 290, such as depicted in FIG. 2. Thus, the DBL may be formed as a combination reagent/DBL on the conductor, as a distinct layer on the conductor, or as a distinct layer on the reagent layer. When the working electrode 175 includes the distinct DBL 290, the reagent layer 275 may or may not reside on the DBL 290. Instead of residing on the DBL 290, the reagent layer 275 may reside on any portion of the sensor strip 100 that allows the reagent to solubilize in the sample. For example, the reagent layer 175 may reside on the base 110 or on the lid 120.

The DBL provides a porous space having an internal volume where a measurable species may reside. The pores of the DBL may be selected so that the measurable species may diffuse into the DBL, while physically larger sample constituents, such as RB cells, are substantially excluded. Although conventional sensor strips have used various materials to filter RB cells from the surface of the working electrode, a DBL provides an internal porous space to contain and isolate a portion of the measurable species from the sample.

When the reagent layer 275 includes a water-soluble binder, any portion of the binder that does not solubilize into the sample prior to the application of an excitation may function as an integral DBL. The average initial thickness of a combination DBL/reagent layer is preferably less than 30 or 23 micrometers (μm) and more preferably less than 16 μm. At present, an especially preferred average initial thicknesses of a combination DBL/reagent layer is from 1 to 30 μm or from 3 to 12 μm. The desired average initial thickness of a combination DBL/reagent layer may be selected for a specific excitation length on the basis of when the diffusion rate of the measurable species from the DBL to a conductor surface, such as the surface of the conductor 170 or the surface of the surface conductor 270 from FIG. 2, becomes relatively constant.

Furthermore, using too thick of a DBL with a short excitation length may delay when the diffusion rate of the measurable species from the DBL to the conductor surface becomes relatively constant. For example, when duty cycles including sequential 1 second excitations separated by 0.5 second relaxations are applied to a working electrode using a combination DBL/reagent layer having an average initial thickness of 30 μm, a preferred diffusion rate may not be reached until at least 6 duty cycles have been applied (>~10 seconds). Conversely, when the same duty cycles are applied to a working electrode using a combination DBL/reagent layer having an average initial thickness of 11 μm, a relatively constant diffusion rate may be reached after the second excitation (~2.5 seconds). Thus, there is an upper limit for the preferred average initial thickness of the DBL for a given duty cycle. A more in-depth treatment of the correlation between DBL thickness, excitation length, and time to reach a relatively constant diffusion rate may be found in U.S. Provisional App. No. 60/655,180, filed Feb. 22, 2005, entitled "Concentration Determination in a Diffusion Barrier Layer".

The distinct DBL 290 may include any material that provides the desired pore space, while being partially or slowly soluble in the sample. In one aspect, the distinct DBL 290 may include a reagent binder material lacking reagents. The distinct DBL 290 may have an average initial thickness of at least 5 μm, preferably, from 8 to 25 μm, and more preferably from 8 to 15 μm.

Figure 3:
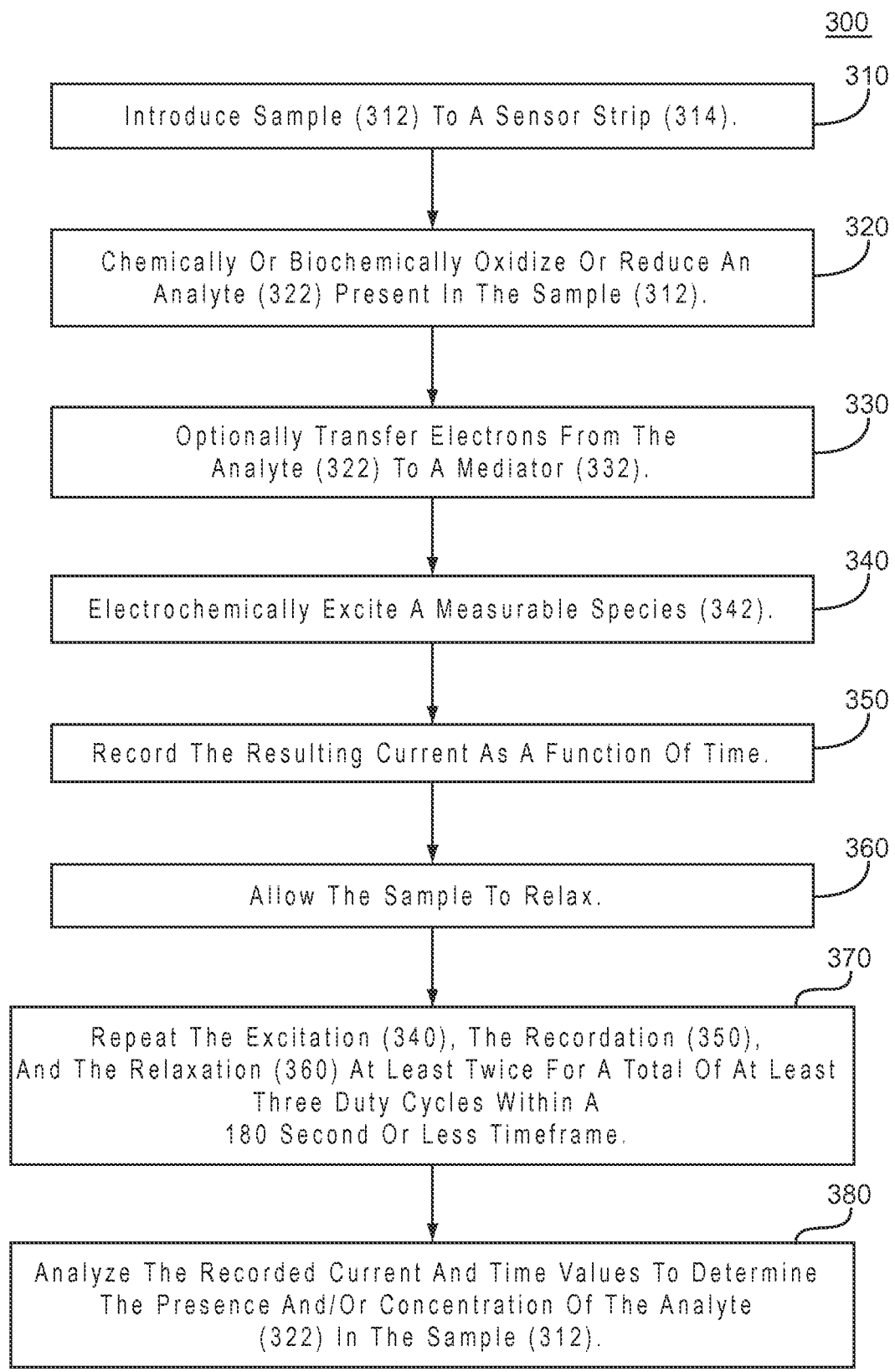
FIG. 3 represents an electrochemical analytic method of determining the presence and concentration of an analyte in a sample.

FIG. 3 represents an electrochemical analysis 300 for determining the presence and optionally the concentration of an analyte 322 in a sample 312. In 310, the sample 312 is introduced to a sensor strip 314, such as the sensor strip depicted in FIGS. 1A-1B and 2. The reagent layers, such as 275 and/or 285 from FIG. 2, begin to solubilize into the sample 312, thus allowing reaction. At this point in the analysis, it may be beneficial to provide an initial time delay, or "incubation period," for the reagents to react with the sample 312. Preferably, the initial time delay may be from 1 to 10 seconds. A more in-depth treatment of initial time delays may be found in U.S. Pat. Nos. 5,620,579 and 5,653,863.

During the reaction, a portion of the analyte 322 present in the sample 312 is chemically or biochemically oxidized or reduced in 320, such as by an oxidoreductase. Upon oxidation or reduction, electrons optionally may be transferred between the analyte 322 and a mediator 332 in 330.

In 340, a measurable species 342, which may be the charged analyte 322 from 320 or the charged mediator 332 from 330, is electrochemically excited (oxidized or reduced). For example, when the sample 312 is whole blood containing glucose that was oxidized by glucose oxidase in 320, which then transfers an electron to reduce a ferricyanide (III) mediator to ferrocyanide (II) in 330, the excitation of 340 oxidizes ferrocyanide (II) to ferricyanide (III) at the working electrode. In this manner, an electron is selectively transferred from the glucose analyte to the working electrode of the sensor strip where it may be detected by a measuring device.

The current resulting from the excitation 340 may be recorded during the excitation 340 as a function of time in 350. In 360, the sample undergoes relaxation. Preferably, the current is not recorded during the relaxation 360.

In 370, the excitation 340, the recordation 350, and the relaxation 360 are repeated at least twice for a total of at least three duty cycles within a 180 second or less timeframe. The recorded current and time values may be analyzed to determine the presence and/or concentration of the analyte 322 in the sample 312 in 380.

Amperometric sensor systems apply a potential (voltage) to the sensor strip to excite the measurable species while the current (amperage) is monitored. Conventional amperometric sensor systems may maintain the potential while measuring the current for a continuous read pulse length of from 5 to 10 seconds, for example. In contrast to conventional methods, the duty cycles used in the electrochemical analysis 300 replace continuous, long-duration read pulses with multiple excitations and relaxations of short duration.

Figure 4A:
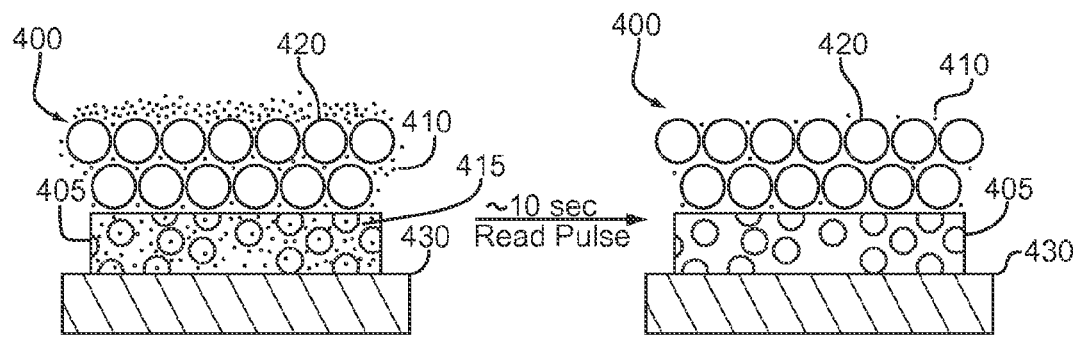
FIGS. 4A and 4B depict a working electrode having a surface conductor and a DBL during the application of long and short read pulses.
Figure 4B:
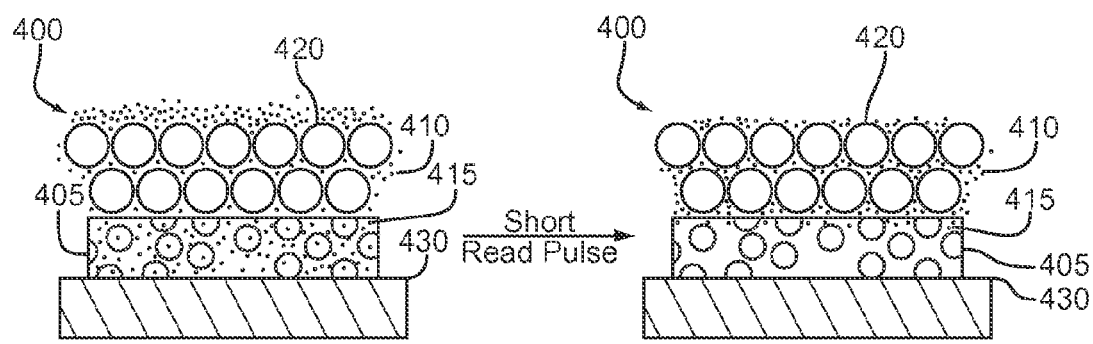

The analysis 300 may increase the accuracy and/or precision of the analyte determination when the measurable species excited at the working electrode in 540 is substantially drawn from the interior of a DBL, as opposed to the measurable species present in the cap-gap of the strip. FIGS. 4A and 4B depict a working electrode 400 having a surface conductor 430 and a distinct DBL 405 during the application of a long read pulse and a short excitation. When a WB sample is applied to the working electrode 400, RB cells 420 cover the DBL 405. Analyte present in the sample forms external measurable species 410 external to the DBL 405. A portion of the external measurable species 410 diffuses into the distinct DBL 405 to give internal measurable species 415.

As shown in FIG. 4A, when a continuous 10 second read pulse is applied to the working electrode 400, both the external and internal measurable species 410 and 415 are excited at the surface conductor 430 by a change in oxidation state. During the long read pulse, the external measurable species 410 diffuses through the sample region where the RB cells 420 reside and through the DBL 405 to the surface conductor 430. Diffusion of the external measurable species 410 through the RB cells 420 during the read pulse introduces the hematocrit effect to the analysis. Because a substantial portion of the measurable species excited at the surface conductor 430 originates from outside the DBL 420, a long read pulse applied to a sensor strip having a DBL may perform similarly with regards to the hematocrit effect to a short read pulse applied to a strip lacking a DBL.

Conversely, FIG. 4B represents the situation where a short excitation is applied to the DBL equipped sensor strip 400 to excite the internal measurable species 415, while substantially excluding from excitation the measurable species 410 external to the DBL 405. During the short excitation, the measurable species 410 either remains external to the DBL 405 or does not substantially diffuse through the DBL to reach the surface conductor 430. In this manner, the short excitation may provide a substantial reduction in the influence of the hematocrit effect on the analysis.

By controlling the length of excitation at the working electrode, the measurable species internal to the DBL may be analyzed, while the measurable species external to the DBL may be substantially excluded from analysis. In relation to the surface conductor 430 of the working electrode, the thickness and internal volume of the DBL 405 is believed to alter the diffusion rate of the internal measurable species 415 in relation to the diffusion rate of the external measurable species 410.

Because the measurable species internal to the DBL may diffuse at a different rate to the conductor of the working electrode than the measurable species external to the DBL, the length of the excitation at the working electrode may select which measurable species is preferentially analyzed. While identical from a molecular standpoint, the different diffusion rates of the measurable species internal and external to the DBL may allow differentiation.

While not wishing to be bound by any particular theory, it is presently believed that the rate of diffusion of the measurable species from outside the DBL into the DBL is varying, while the diffusion rate of the measurable species from the internal volume of the DBL to the conductor is relatively constant. The varying rate of diffusion of the measurable species outside the DBL may be caused by the RB cells and other constituents present in the sample and may give rise to the hematocrit effect. Thus, analysis errors (bias) introduced by the sample constituents, including RB cells, may be reduced by substantially limiting analysis to the measurable species having a relatively constant diffusion rate to the conductor.

Another advantage of selectively analyzing the measurable species internal to the DBL is a reduction of measurement imprecision from sensor strips having varying cap-gap volumes. If a read pulse continues past the time when substantially all of the measurable species present in the cap-gap has been analyzed, the analysis no longer represents the concentration of measurable species in the sample, but has instead determined the amount of measurable species in the cap-gap; a very different measurement. As the excitation length becomes long relative to the volume of the cap-gap, the current measurement will depend on the volume of the cap-gap, not the underlying analyte concentration. Thus, long read pulses may result in measurements that are highly inaccurate with regard to analyte concentration when the pulse length "overshoots" the measurable species present in the cap-gap.

As described in U.S. Provisional App. No. 60/617,889, filed Oct. 12, 2004, entitled "Concentration Determination in a Diffusion Barrier Layer," a single short read pulse or excitation may be selected to substantially limit measurable species excitation to a DBL. When a single excitation is used, the length of the excitation and the thickness of the DBL may be preferably selected so that a relatively constant diffusion rate of the measurable species from the DBL to the conductor surface is reached during the excitation. If a relatively constant diffusion rate is not reached during the excitation, the concentration of the measurable species within the DBL may not accurately represent the concentration of the measurable species in the sample, thus adversely affecting the analysis. Furthermore, the single excitation may not effectively reduce the background signal from the mediator.

Referring to FIG. 3, the excitation 340, the recordation 350, and the relaxation 360 constitute a single duty cycle, which may be applied to a sensor strip at least three times during a 180 second or less time period. More preferably, at least 4, 6, 8, 10, 14, 18, or 22 duty cycles are applied during an independently selected 120, 90, 60, 30, 15, 10, or 5 second time period. In one aspect, the duty cycles are applied during a 5 to 60 second time period. In another aspect, from 3 to 18 or from 3 to 10 duty cycles may be applied within 30 seconds or less. In another aspect, from 4 to 8 duty cycles may be applied within 3 to 16 seconds.

The potential applied during the excitation 340 portion of the duty cycle is preferably applied at a substantially constant voltage and polarity throughout its duration. This directly contrasts to conventional read pulses where the voltage is changed or "swept" through multiple voltage potentials and/or polarities during data recordation. In one aspect, the duration of the excitation 340 is at most 4 or 5 seconds, and preferably less than 3, 2, 1.5, or 1 second. In another aspect, the duration of the excitation 340 is from 0.01 to 3 seconds, from 0.01 to 2 seconds, or from 0.01 to 1.5 seconds. More preferably, the duration of the excitation 340 is from 0.1 to 1.2 seconds.

After the excitation 340, in 360 the measuring device may open the circuit through the sensor strip 314, thus allowing the system to relax. During the relaxation 360, the current present during the excitation 340 is substantially reduced by at least one-half, preferably by an order of magnitude, and more preferably to zero. Preferably, a zero current state is provided by an open circuit or other method known to those of ordinary skill in the art to provide a substantially zero current flow. At least 3 relaxations may be provided during the duty cycles of the pulse sequence.

In one aspect, the relaxation 360 is at least 10, 5, 3, 2, 1.5, 1, or 0.5 seconds in duration. In another aspect, the relaxation 360 is from 0.1 to 3 seconds, from 0.1 to 2 seconds, or from 0.1 to 1.5 seconds in duration. More preferably, the relaxation 360 is from 0.2 to 1.5 seconds in duration and provided by an open circuit.

During the relaxation 360, the ionizing agent may react with the analyte to generate additional measurable species without the effects of an electric potential. Thus, for a glucose sensor system including glucose oxidase and a ferricyanide mediator as reagents, additional ferrocyanide (reduced mediator) responsive to the analyte concentration of the sample may be produced without interference from an electric potential during the relaxation 360.

Many conventional analysis methods continuously apply a voltage during the duration of the read pulse. The applied voltage may have a fixed potential or may have a potential that is swept from a positive to a negative potential or from a positive or a negative potential to a zero potential relative to a potential. Even at a zero relative potential, these methods continuously draw current from the sensor strip during the read pulse, which permits the electrochemical reaction to continue throughout the read pulse. Thus, the reaction that produces measurable species responsive to the analyte concentration and the diffusion of the measurable species to the working electrode are both affected by current during the zero potential portion of a conventional read pulse.

Conventional methods that continuously apply voltage to and draw current from the sensor strip, even at a zero potential in relation to a potential, are fundamentally different from the relaxations of the present invention. The multiple duty cycles applied by the present invention also are markedly different from conventional methods that use a single long duration pulse with multiple measurements, such as those disclosed in U.S. Pat. No. 5,243,516, due to the multiple relaxations of the present invention. In contrast to these conventional methods, each duty cycle of the pulse sequences of the present invention provides an independent diffusion and analyte reaction time during the relaxation.

Figure 5A:
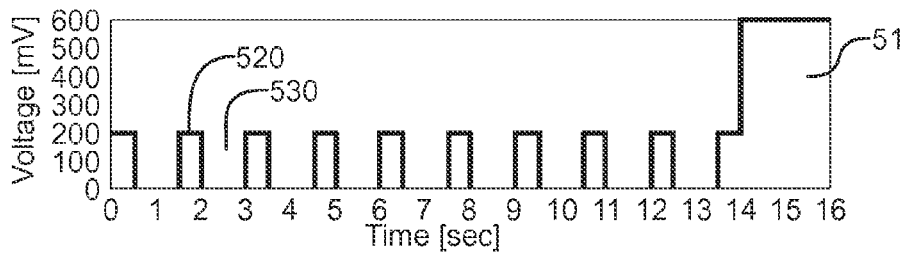
FIGS. 5A-5E represent five examples of pulse sequences where multiple duty cycles were applied to the sensor strip after introduction of the sample.
Figure 5B:
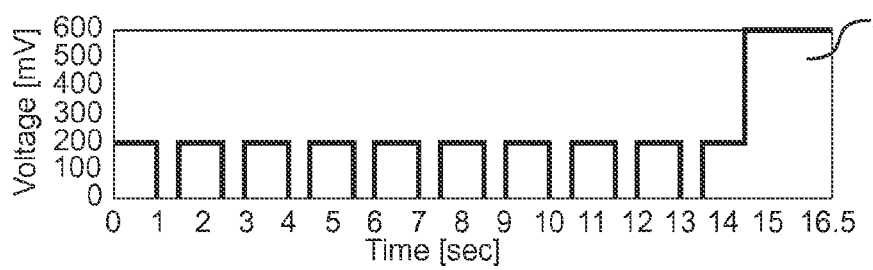
Figure 5C:
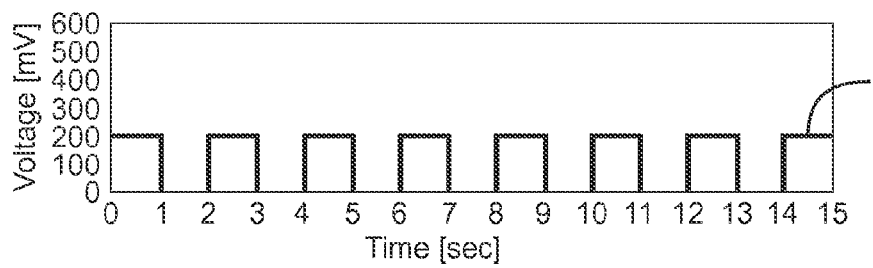
Figure 5D:
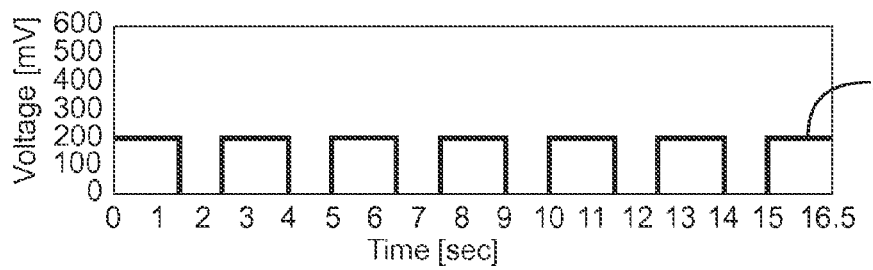

FIGS. 5A-5E depict five examples of gated amperometric pulse sequences where multiple duty cycles were applied to the sensor strip after introduction of the sample. In these examples, square-wave pulses were used; however, other wave types compatible with the sensor system and the test sample also may be used. FIGS. 5C-5D depict pulse sequences including multiple duty cycles having the same excitation and open circuit delay times.

FIGS. 5A-5B depict pulse sequences that include 9 duty cycles having the same excitation and open circuit delay times in addition to a terminal read pulse 510 of longer duration that increases in voltage. The increased voltage of this terminal read pulse provides the ability to detect a species having a higher oxidation potential. A more complete discussion regarding terminal read pulses may be found in U.S. Provisional App. No. 60/669,729, filed Apr. 8, 2005, entitled "Oxidizable Species as an Internal Reference in Control Solutions for Biosensors."

Figure 5E:
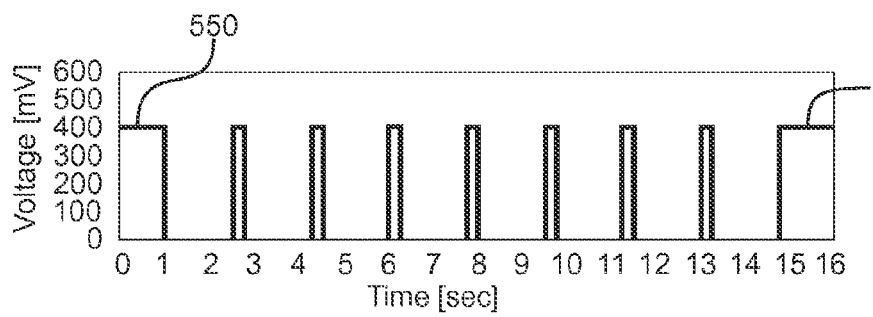

FIG. 5A depicts a 9 duty cycle pulse sequence where 0.5 second excitations are separated by 1 second open circuit delays to give a redox intensity (RI) of 0.357 (5/14). Thus, in FIG. 5A, the second duty cycle has an excitation portion 520 and a relaxation portion 530. FIG. 5B depicts a 9 duty cycle pulse sequence where 1 second excitations are separated by 0.5 second open circuit delays to give a RI of 0.69 (10/14.5). FIG. 5C depicts an 7 duty cycle pulse sequence where 1 second excitations are separated by 1 second open circuit delays to give a RI of 0.53 (8/15). A terminal read pulse 540 of the same duration and voltage as those used during the 7 duty cycles was applied. FIG. 5D depicts a 6 duty cycle pulse sequence where 1.5 second excitations are separated by 1 second open circuit delays to give a RI of 0.636 (10.5/16.5). As in FIG. 5C, the terminal read pulse 540 of the same duration and voltage as the prior duty cycle pulses was applied. FIG. 5E depicts a 7 duty cycle pulse sequence where relatively short 0.25 second excitations are separated by relatively long 1.5 second relaxations. The FIG. 5E pulse sequence begins with an initial 1 second pulse 550 and ends with the 1.25 second terminal read pulse 540 to provide a RI of 0.25 (4/16).

The higher the RI for a pulse sequence, the less background will be introduced into the analysis by the mediator. The pulse sequences represented in FIGS. 5A-5E are oxidative pulses, designed to excite (i.e. oxidize) a reduced mediator, which is the measurable species. Thus, the greater the oxidative current applied to the sensor strip in a given time period, the less chance that mediator reduced by pathways other than oxidation of the analyte is contributing to the recorded current values.

Table III, below, provides the slope, intercept, and ratio of intercept-to-slope for the contour profiles of the last four duty cycles of pulse sequences (a) and (b). Pulse sequence (a) was:

9×(0.5 sec on+1.0 sec off)+0.5 sec=14 sec, RI=5/14=0.357.

Pulse sequence (b) was:

9×(1.0 sec on+0.375 sec off)+1.0 sec=13.375 sec, RI=10/13.375=0.748

TABLE III

| | Pulse Sequence (a), RI = 0.357 | | | Pulse Sequence (b), RI = 0.748 | | |
|---|---|---|---|---|---|---|
| Pulse # | Slope | Intercept | Int/Slope | Slope | Intercept | Int/Slope |
| 7 | 20.5 | 2581.6 | 125.93 | 14.07 | 741.29 | 52.69 |
| 8 | 19.99 | 2239.4 | 112.03 | 13.47 | 649.93 | 48.25 |
| 9 | 19.53 | 1973.4 | 101.04 | 12.92 | 580.94 | 44.96 |
| 10 | 19.1 | 1762.5 | 92.28 | 12.45 | 525.26 | 42.19 |

The intercept-to-slope ratios provide an indication of the amount of background signal attributable to the mediator, with higher ratio values indicating a greater proportion of the recorded signal attributable to mediator background. Thus, while the pulse frequency (number of excitations/total assay time in seconds) of sequences (a) and (b) are similar at about 0.7 sec-1, the increase in RI provided by pulse sequence (b) provides less than half as much background signal. In combination, the multiple excitations of the pulse sequence may eliminate the need for an initial pulse to renew the oxidation state of the mediator. While the background current may be influenced by the mediator, for ferricyanide, pulse sequences having RI values of at least 0.01, 0.3, 0.6, or 1 are preferred, with RI values of from 0.1 to 0.8, from 0.2 to 0.7, or from 0.4 to 0.6 being more preferred.

Figure 6A:
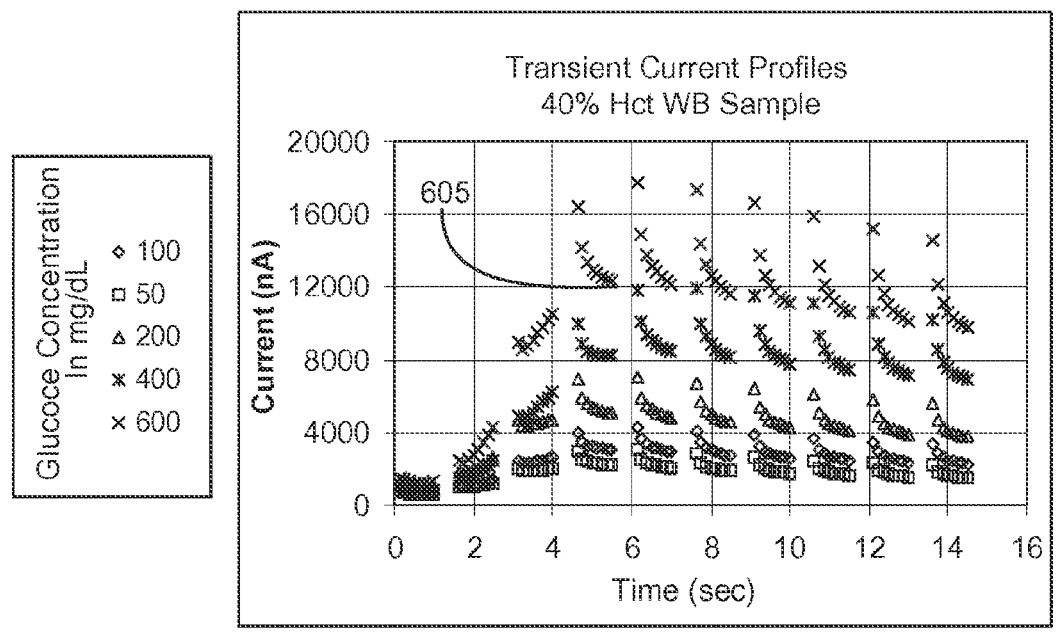
FIG. 6A shows the transient output currents of the pulse sequence represented in FIG. 5B for 40% hematocrit WB samples containing 50, 100, 200, 400, and 600 mg/dL glucose.

Referring back to FIG. 3, in 350 the current passing through the conductors of the sensor strip 314 for each duty cycle of the pulse sequence may be recorded as a function of time. FIG. 6A shows the output currents plotted as a function of time for the pulse sequence represented in FIG. 5B for 40% hematocrit WB samples containing 50, 100, 200, 400, and 600 mg/dL glucose. Instead of a conventional long duration read pulse resulting in extensive oxidation of the measurable species, each excitation is followed by a break in the current profile.

In FIG. 6A, when the output currents are plotted as a function of time, each excitation results in a transient current profile having an initial high current value that decays over time. Preferably, the duty cycles include short, independent excitations and relaxations that inhibit the system from reaching a steady-state or a slow current decay condition during each excitation, as required during the read pulse of conventional systems. Instead of conventional steady-state or slowly decaying currents, transient (rapidly decaying) current values are obtained from the gated amperometric pulse sequences because the electrochemical reaction of the measurable species at the working electrode is faster than the rate at which the measurable species is supplied to the working electrode by diffusion.

Figure 6B:
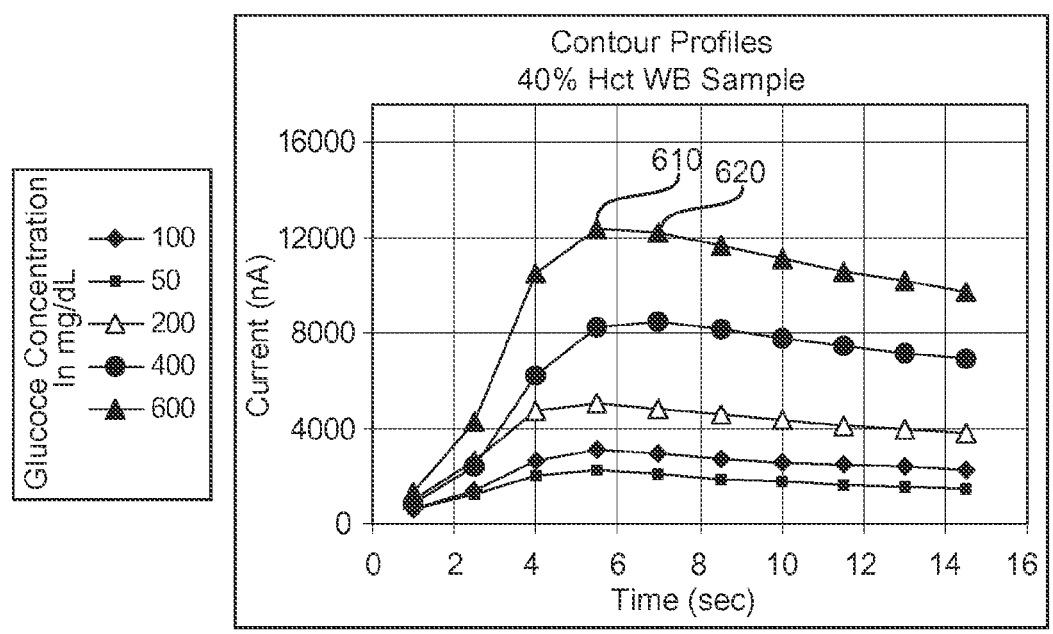
FIG. 6B shows current contour profiles prepared by plotting and connecting the final current value from each of the transient current profiles shown in FIG. 6A.

FIG. 6B shows a contour profile plot prepared by connecting the final current value from each of the transient current profiles (i.e. the final current value from each excitation) shown in FIG. 6A. The contour profile may be used to simulate the data obtained from a conventional system at steady-state, where the current change with time is substantially constant.

The transient current profiles obtained from gated amperometric pulse sequences and the derived contour current values are fundamentally different from the current profiles obtained from a conventional analysis using a single read pulse. While currents recorded from a single read pulse derive from a single relaxation/diffusion, each time point in the contour profile of the transient currents originates from an excitation after an independent relaxation/diffusion process. Furthermore, as the length of an excitation increases, the correlation between the current and the analyte concentration may decrease, often due to the hematocrit effect. Thus, the accuracy of an analysis using multiple, short excitations may be increased in comparison to an analysis using a longer read pulse having the duration of the multiple excitations combined.

Referring back to FIG. 6A, a transient point 605 is reached in the current profile when the last in time current value obtained for an excitation represents the greatest last in time current value obtained for any excitation. Thus, for FIG. 6A the transient point is reached at approximately 5 seconds. For each of the glucose concentrations, equilibrium with regards to DBL re-hydration may be reached at the highest current value in the contour profile for each glucose concentration. Thus, when the transient currents of FIG. 6A are converted to contour currents in FIG. 6B, reading 610 (highest) and 620 (lower) establish that equilibrium was reached regarding diffusion of the measurable species into the DBL and re-hydration of the DBL at about five seconds for the 600 mg/dL glucose concentration.

Current values recorded at a relatively constant diffusion rate minimize inaccuracies that would otherwise be introduced by variations in the rehydration and diffusion rates of the reagents. Thus, once a relatively constant diffusion rate is reached, the recorded current values more accurately correspond to the concentration of the measurable species, and thus the analyte. Furthermore, for FIG. 6B, the complete analysis may be completed in as few as seven seconds because once the highest current value 610 of the contour profile is known, its value may be directly correlated to the analyte concentration. Additional data points may be obtained to reduce background error attributable to the mediator, as previously discussed.

Figure 6C:
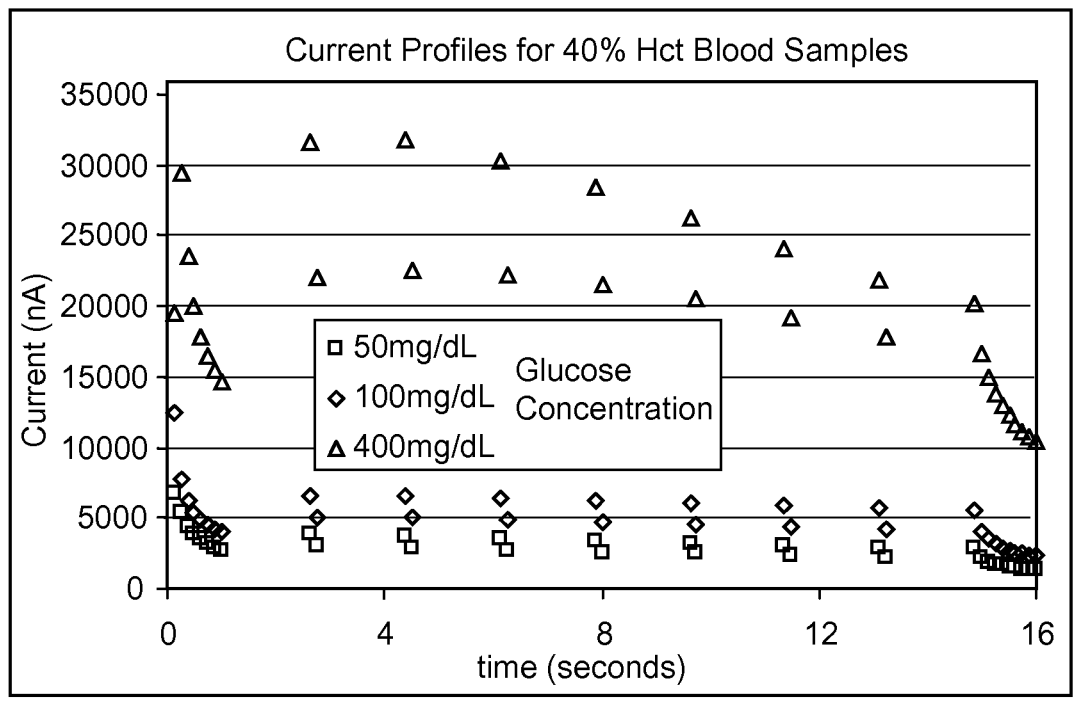
FIG. 6C shows current contour profiles prepared from transient current profiles generated by the pulse sequence depicted in FIG. 5E.

FIG. 6C shows current contour profiles prepared from transient current profiles generated by the pulse sequence depicted in FIG. 5E. During each 0.25 second excitation, current values were recorded at the middle (~0.125 second) and end (~0.25 second), which may be used to determine a decay constant. Using the longer initial pulse with the short excitations and relatively long relaxations, the analysis may be completed in about four seconds.

Figure 6D:
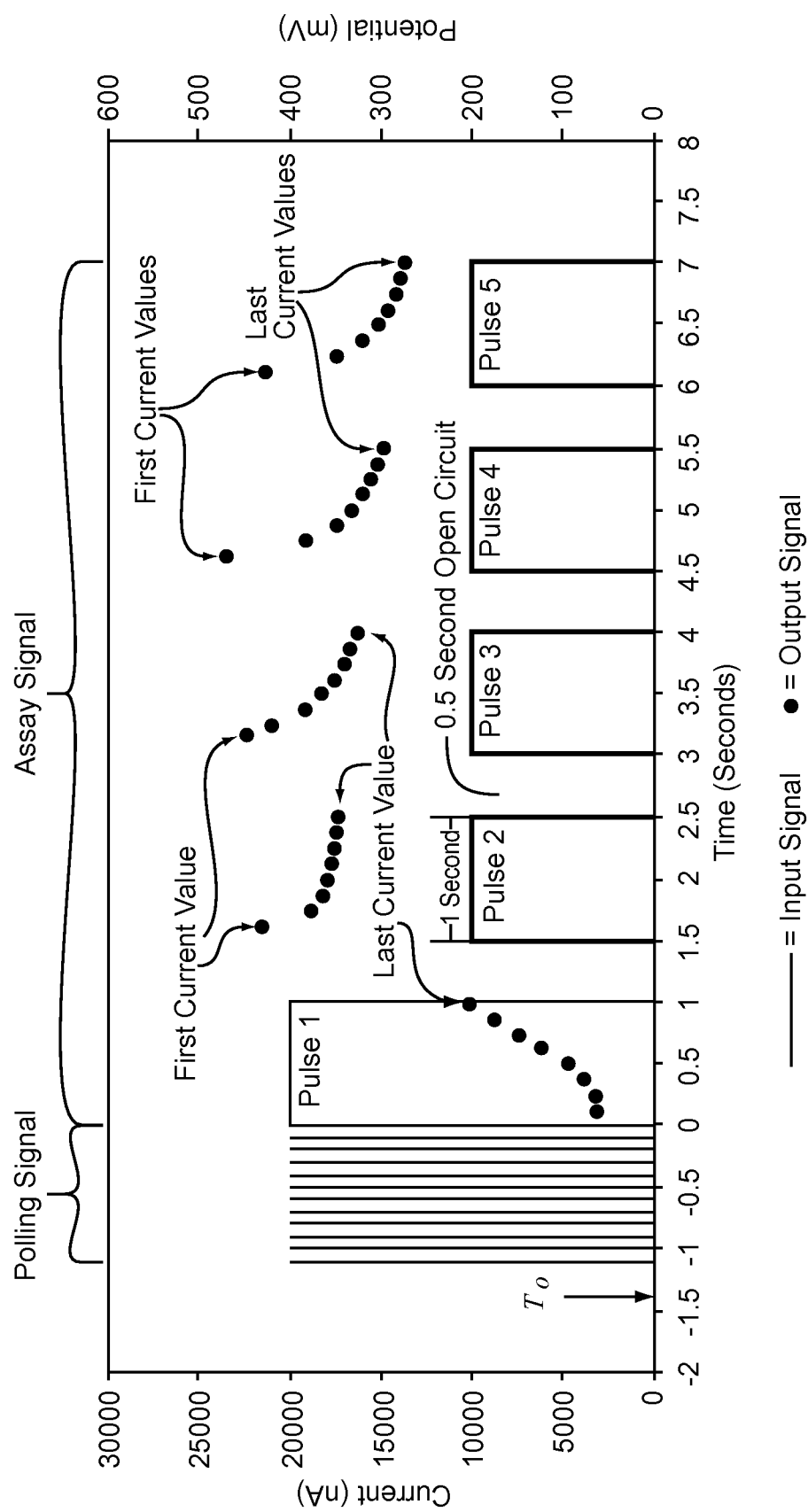
FIG. 6D is a graph illustrating output signals in relation to input signals for an electrochemical system using gated amperometric pulse sequences.

FIG. 6D is a graph illustrating output signals in relation to input signals for an electrochemical system using gated amperometric pulse sequences. The input signals are potentials applied to a sample of biological fluid. The input signals include a polling input signal and an assay input signal. The output signals are currents generated from the sample. The output signals include a polling output signal and an assay output signal. The sample generates the assay output signal from a redox reaction of glucose in whole blood in response to the assay input signal. The input and output signals may be for a biosensor having working and counter electrodes. Other biosensors may be used including those with additional electrodes and different configurations. Other analyte concentrations may be measured including those in other biological fluids. Other output signals may be generated including those that decline initially and those that decline in all pulses.

In use, a sample of the biological fluid is deposited in a biosensor. The biosensor applies a polling signal to the sample from about −1.25 seconds through about 0 seconds. The pulses have a pulse width of about 5-10 ms and a pulse interval of about 125 ms. The biosensor generates a polling output signal in response to the polling input signal. The biosensor measures the polling output signal. The biosensor may have a potentiostat that provides the polling output signal to the input of an analog comparator.

When the polling output signal is equal to or greater than a polling threshold, the biosensor applies the assay input signal to the electrodes from about 0 seconds through about 7 seconds. The polling threshold valve may be about 250 nA. The comparator may compare the polling output signal to the polling threshold value. When the polling output signal exceeds the polling threshold value, the output signal of the comparator may trigger the launch of the assay input signal.

During the assay input signal, the biosensor applies a duty cycle with a first pulse having a potential of about 400 mV for about 1 sec to the working and counter electrodes. The first pulse is followed by a 0.5 sec relaxation, which may be an essentially open circuit or the like. The assay output signal or current within the first pulse is measured and stored in a memory device. The biosensor may apply a second pulse to the working and counter electrodes at about 200 mV for about 1 sec. The assay output signal or current within the second pulse is measured and stored in a memory device. The biosensor continues applying pulses from the assay input signal to the working and counter electrodes until the end of the assay period or for as long as desired by the biosensor. The assay period may be about 7 seconds. The biosensor may measure and store assay output signal or current within each pulse.

The polling input signal is an electrical signal, such as current or potential, that pulses or turns on and off at a set frequency or interval. The sample generates a polling output signal in response to the polling input signal. The polling output signal is an electrical signal, such as current or potential. The biosensor may show the polling output signal on a display and/or may store the assay output signal in a memory device. The biosensor may apply the polling signal to detect when a sample connects with the electrodes. The biosensor may use other methods and devices to detect when a sample is available for analysis.

The polling input signal is duty cycle in which a sequence of polling pulses is separated by polling relaxations. During a polling pulse, the electrical signal is on. During a polling relaxation, the electrical signal is off. On may include time periods when an electrical signal is present. Off may include time periods when an electrical signal is not present. Off may not include time periods when an electrical signal is present but has essentially no amplitude. The electrical signal may switch between on and off by closing and opening an electrical circuit, respectively. The electrical circuit may be opened and closed mechanically, electrically, or the like.

A polling input signal may have one or more polling pulse intervals. A polling pulse interval is the sum of a polling pulse and a polling relaxation. Each polling pulse has an amplitude and a polling pulse width. The amplitude indicates the intensity of the potential, the current, or the like of the electrical signal. The amplitude may vary or be a constant during the polling pulse. The polling pulse width is the time duration of a polling pulse. The polling pulse widths in a polling input signal may vary or be essentially the same. Each polling relaxation has a polling relaxation width, which is the time duration of a polling relaxation. The polling relaxation widths in a polling input signal may vary or be essentially the same.

The polling input signal may have a polling pulse width of less than about 300 milliseconds (ms) and a polling pulse interval of less than about 1 sec. The polling input signal may have a polling pulse width of less than about 100 ms and a polling pulse interval of less than about 500 ms. The polling input signal may have a polling pulse width in the range of about 0.5 ms through about 75 ms and a polling pulse interval in the range of about 5 ms through about 300 ms. The polling input signal may have a polling pulse width in the range of about 1 ms through about 50 ms and a polling pulse interval in the range of about 10 ms through about 250 ms. The polling input signal may have a polling pulse width of about 5 ms and a polling pulse interval of about 125 ms. The polling input signal may have other pulse widths and pulse intervals.

The biosensor may apply the polling input signal to the sample during a polling period. The polling period may be less than about 15 minutes, 5 minutes, 2 minutes, or 1 minute. The polling period may be longer depending upon how a user uses the biosensor. The polling period may be in the range of about 0.5 second (sec) through about 15 minutes. The polling period may be in the range of about 5 sec through about 5 minutes. The polling period may be in the range of about 10 sec through about 2 minutes. The polling period may be in the range of about 20 sec through about 60 sec. The polling period may be in the range of about 30 through about 40 sec. The polling period may have less than about 200, 100, 50, or pulse intervals. The polling period may have from about 2 through about 150 pulse intervals. The polling period may have from about 5 through about 50 pulse intervals. The polling period may have from about 5 through about 15 pulse intervals. The polling period may have about 10 pulse intervals. Other polling periods may be used.

The biosensor applies the assay input signal when the polling output signal is equal to or greater than a polling threshold. The polling threshold may be greater than about 5 percent (%) of the expected assay input signal at the beginning of the first pulse. The polling threshold may be greater than about 15% of the expected assay input signal at the beginning of the first pulse. The polling threshold may be in the range of about 5 percent (%) through about 50% of the expected assay input signal at the beginning of the first pulse. Other polling thresholds may be used. The biosensor may indicate the polling output signal is equal to or greater than the polling threshold on a display.

The assay input signal is an electrical signal, such as current or potential, that pulses or turns on and off at a set frequency or interval. The sample generates an assay output signal in response to the assay input signal. The assay output signal is an electrical signal, such as current or potential.

The assay input signal is a sequence of assay pulses separated by assay relaxations. During an assay pulse, the electrical signal is on. During an assay relaxation, the electrical signal is off. On includes time periods when an electrical signal is present. Off includes time periods when an electrical signal is not present and does not include time periods when an electrical signal is present but has essentially no amplitude. The electrical signal switches between on and off by closing and opening an electrical circuit, respectively. The electrical circuit may be opened and closed mechanically, electrically, or the like.

An assay input signal may have one or more assay pulse intervals. An assay pulse interval is the sum of an assay pulse and an assay relaxation. Each assay pulse has an amplitude and an assay pulse width. The amplitude indicates the intensity of the potential, the current, or the like of the electrical signal. The amplitude may vary or be a constant during the assay pulse. The assay pulse width is the time duration of an assay pulse. The assay pulse widths in an assay input signal may vary or be essentially the same. Each assay relaxation has an assay relaxation width, which is the time duration of an assay relaxation. The assay relaxation widths in an assay input signal may vary or be essentially the same.

The assay input signal may have an assay pulse width of less than about 5 sec and an assay pulse interval of less than about 15 sec. The assay input signal may have an assay pulse width of less than about 3, 2, 1.5, or 1 sec and an assay pulse interval of less than about 13, 7, 4, 3, 2.5, or 1.5 sec. The assay input signal may have an assay pulse width in the range of about 0.1 sec through about 3 sec and an assay pulse interval in the range of about 0.2 sec through about 6 sec. The assay input signal may have an assay pulse width in the range of about 0.1 sec through about 2 sec and an assay pulse interval in the range of about 0.2 sec through about 4 sec. The assay input signal may have an assay pulse width in the range of about 0.1 sec through about 1.5 sec and an assay pulse interval in the range of about 0.2 sec through about 3.5 sec. The assay input signal may have an assay pulse width in the range of about 0.4 sec through about 1.2 sec and an assay pulse interval in the range of about 0.6 sec through about 3.7 sec. The assay input signal may have an assay pulse width in the range of about 0.5 sec through about 1.5 sec and an assay pulse interval in the range of about 0.75 sec through about 2.0 sec. The assay input signal may have an assay pulse width of about 1 sec and an assay pulse interval of about 1.5 sec. The assay input signal may have other pulse widths and pulse intervals.

The biosensor applies the assay input signal to the sample during an assay period. The assay period may have the same or a different duration than the polling period. The assay period of the assay input signal may be less than about 180, 120, 90, 60, 30, 15, 10, or 5 sec. The assay period may be in the range of about 1 sec through about 100 sec. The assay period may be in the range of about 1 sec through about 25 sec. The assay period may be in the range of about 1 sec through about 10 sec. The assay period may be in the range of about 2 sec through about 3 sec. The assay period may be about 2.5 sec. The assay period may have less than about 50, 25, 20, 15, 10, 8, 6, or 4 assay pulse intervals. The assay period may have assay pulse intervals in the range of about 2 through about 50. The assay period may have assay pulse intervals in the range of about 2 through about 25. The assay period may have assay pulse intervals in the range of about 2 through about 15. The assay period may have about 10 assay pulse intervals. Other assay periods may be used.

Figure 7A:
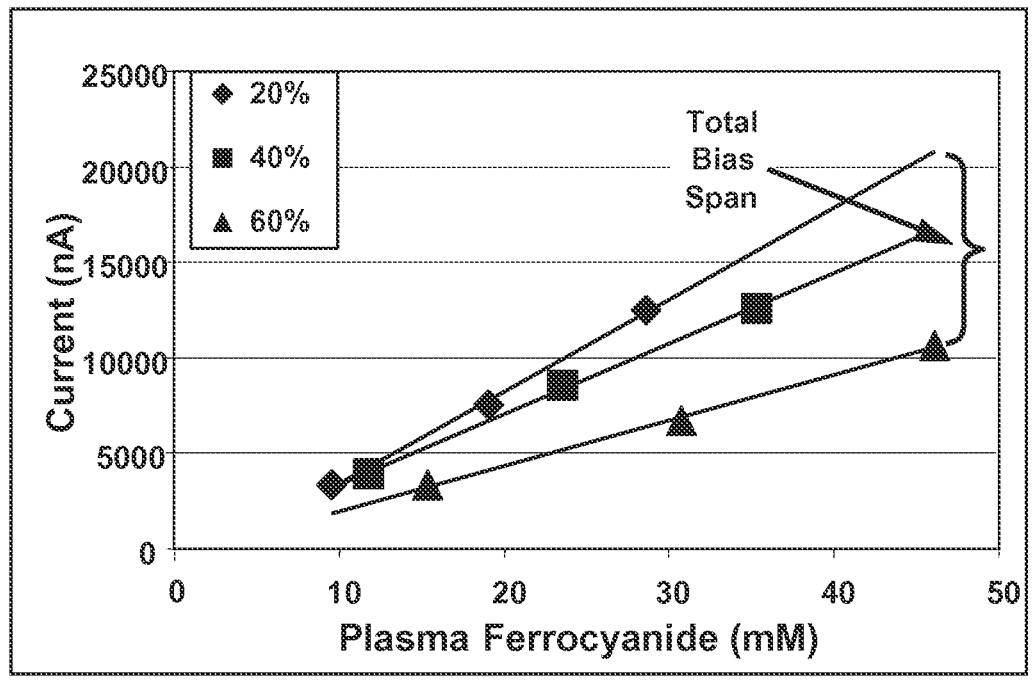
FIGS. 7A and 7B are graphs illustrating the improvement in measurement accuracy when a DBL is combined with a short read pulse.
Figure 7B:
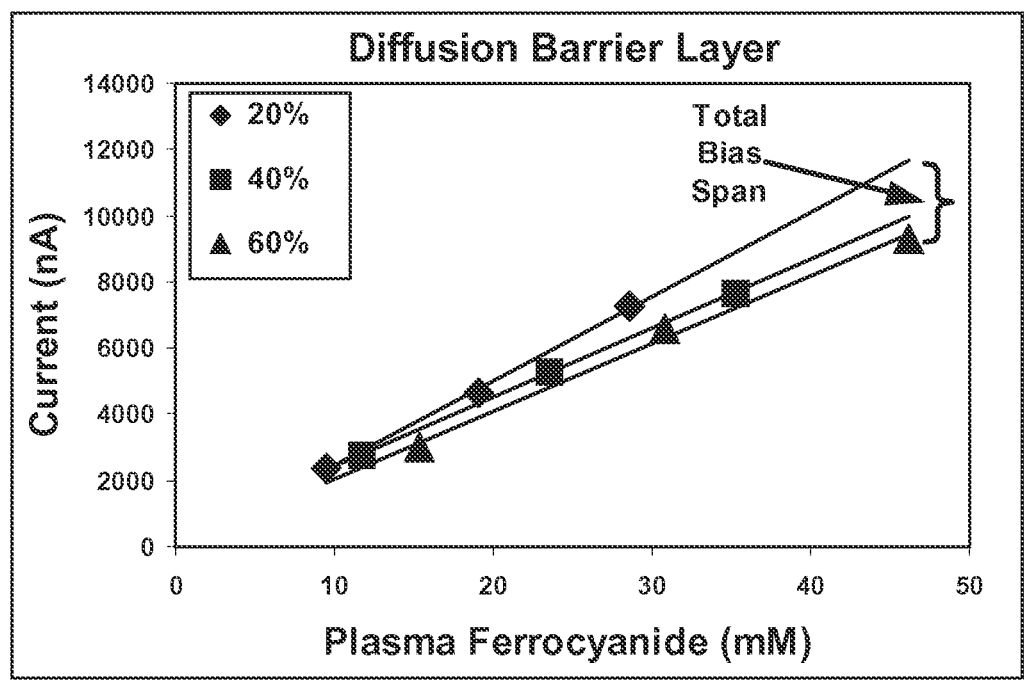

FIGS. 7A and 7B are graphs illustrating the improvement in measurement accuracy when a DBL is combined with a short read pulse. Whole blood samples were combined with ferrocyanide in a 1:5 dilution ratio to represent an underlying glucose concentration and measured with a 1 second read pulse. Thus, the initial 20%, 40%, and 60% hematocrit WB samples were diluted to 16%, 32%, and 48% hematocrit (a 20% reduction of all three hematocrit values). The 20%, 40%, and 60% lines represent the current measured for the blood samples containing 16%, 32%, and 48% hematocrit, respectively.

FIG. 7A shows the inaccuracies introduced by the hematocrit and other effects from a bare conductor sensor strip lacking a DBL. The inaccuracy is represented as the difference between the 20% and 60% hematocrit lines (the total hematocrit bias span) and represents the maximum measurement inaccuracy attributable to the hematocrit effect. Smaller bias values represent a more accurate result. Similar performance was observed when a DBL was used with a longer read pulse as discussed above with regard to FIG. 4A.

Conversely, FIG. 7B shows a marked decrease in the distance between the 20% and 60% calibration lines when a DBL is combined with a 1 second read pulse. A distinct DBL of PEO polymer and 100% KCl (without reagents) was printed on a conductor as used for FIG. 7A above. The total bias hematocrit span with the DBL/short read pulse was nearly two-thirds less than the total bias span without the DBL. Thus, pulse sequences including multiple duty cycles in combination with a DBL may significantly increase measurement accuracy and provide a desirable reduction in mediator background.

Figure 7C:
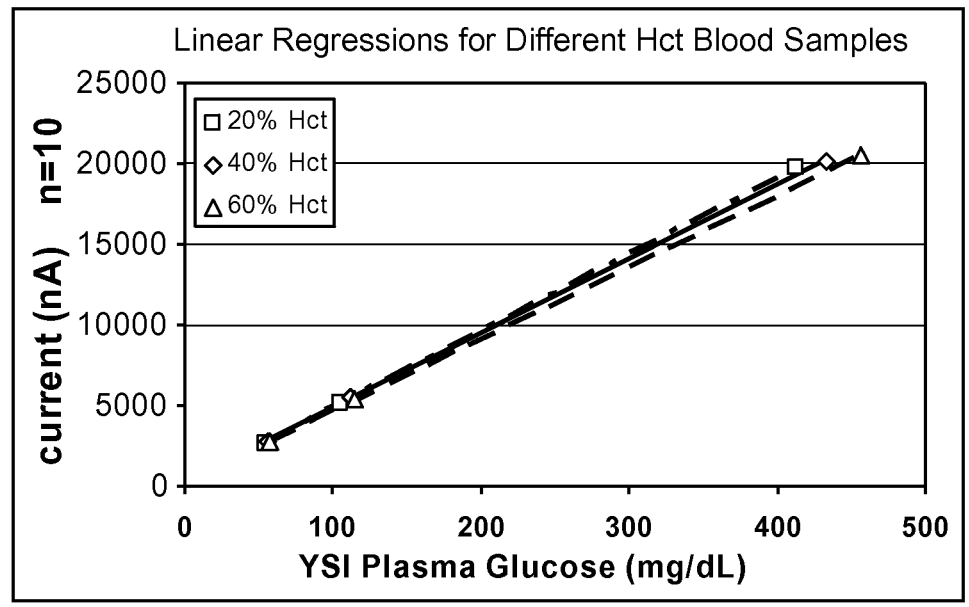
FIGS. 7C and 7D are graphs illustrating the reduction in hematocrit bias that may be obtained when a gated amperometric pulse sequence is combined with a DBL.
Figure 7D:
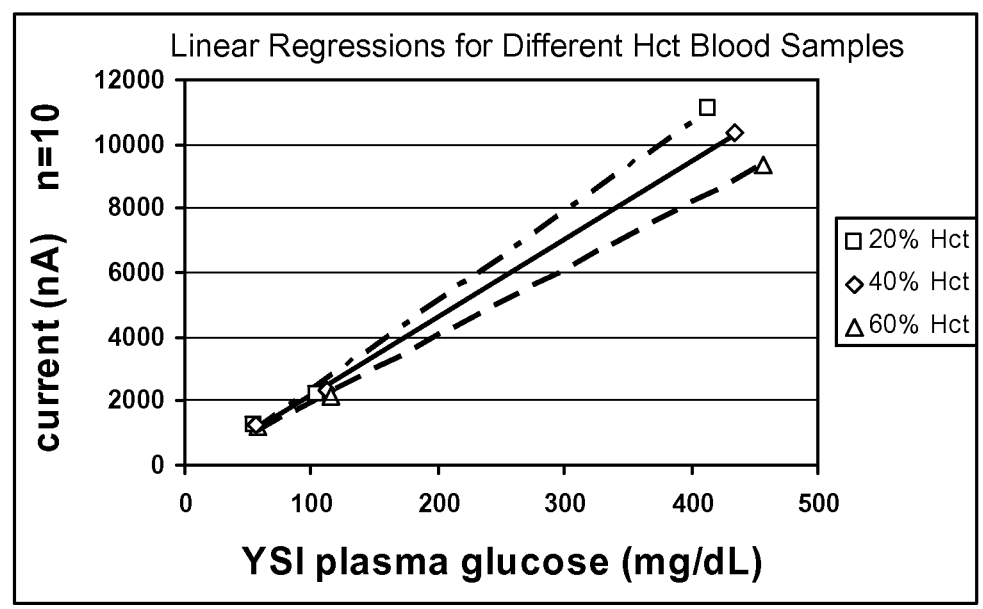

FIGS. 7C and 7D illustrate the reduction in hematocrit bias that may be obtained when a gated amperometric pulse sequence is combined with a DBL. FIG. 7C demonstrates that the measurement bias attributable to hematocrit effect is within ±5% when a DBL was combined with the pulse sequence of FIG. 5E and the current values were recorded at 14.875 seconds or 0.125 seconds from the last pulse. For comparison, FIG. 7D establishes that bias increases to ±15% when current value at 16 seconds (1.25 seconds from the last pulse) is used to determine the glucose concentration of the sample. Thus, the longer the duration of the excitation, the greater the hematocrit bias observed.

In addition to the ability of the present invention to reduce inaccuracy from the hematocrit effect and mediator background signal, the combination of the transient current profile of each excitation and the resulting contour profiles may be used to provide multiple sets of calibration constants to the sensor system, thus increasing the accuracy of the analysis. Each set of calibration constants obtained may be used to correlate a specific current reading to a specific concentration of measurable species in the sample. Thus, in one aspect, an increase in accuracy may be obtained by averaging the glucose values obtained using multiple sets of calibration constants.

Conventional electrochemical sensor systems generally use one set of calibration constants, such as slope and intercept, to convert current readings into corresponding concentration of the analyte in the sample. However, a single set of calibration constants may result in inaccuracies in the analyte concentration determined from the recorded current values because random noise is included in the measurement.

Figure 8:
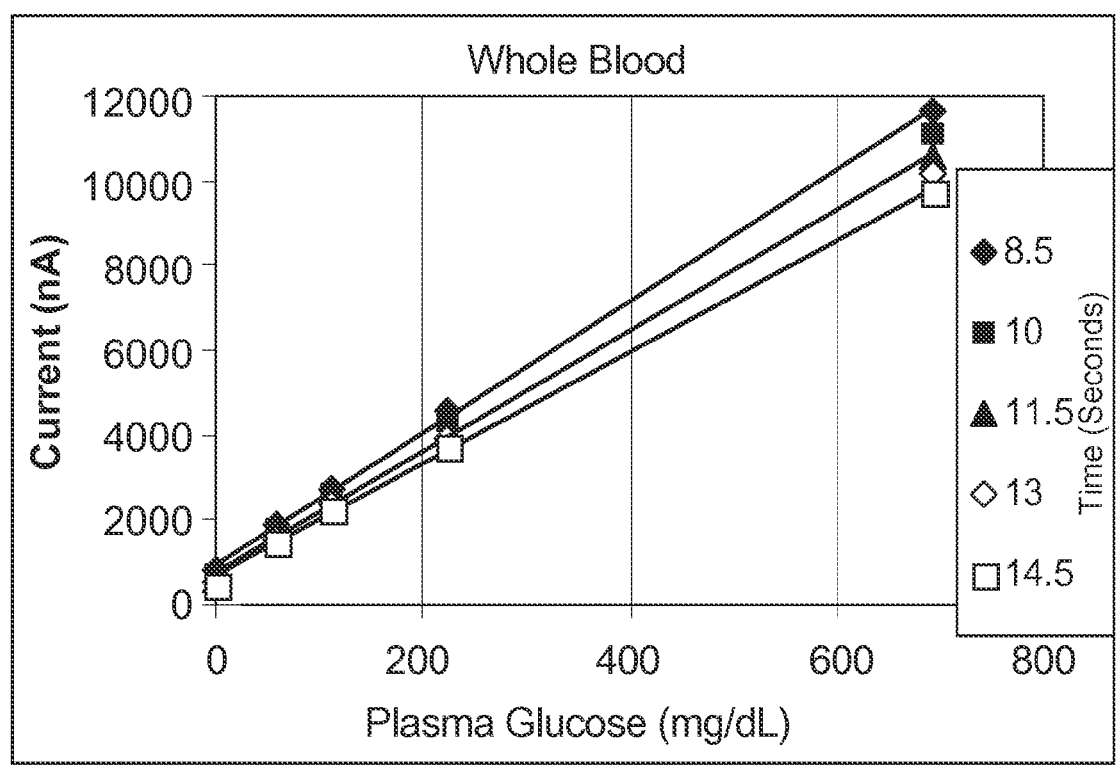
FIG. 8 plots the endpoint currents recorded at multiple duty cycles when the pulse sequence of FIG. 5B was applied to WB samples containing various glucose concentrations.

By taking the current value at a fixed time within each duty cycle of the pulse sequences of the present invention, multiple sets of calibration constants may be established. FIG. 8 plots the endpoint currents recorded at 8.5, 10, 11.5, 13, and 14.5 seconds (duty cycles 6-9 and first portion of the terminal read pulse) when the pulse sequence depicted in FIG. 5B was applied to WB samples containing various glucose concentrations. Each of these five calibration lines are independent of the other and may be used in at least two ways.

First, the multiple sets of calibration constants may be used to determine the number of duty cycles that should be applied during the pulse sequence to obtain the desired accuracy, precision, and assay time. For example, if the current values obtained from the first three excitations indicate a high glucose concentration, such as >150 or 200 mg/dL, the sensor system may terminate the analysis at about 5.5 seconds, thus considerably shortening the time required for the analysis. Such a shortening may be possible because imprecision at high glucose concentrations is typically less than at lower glucose concentrations. Conversely, if the current values obtained from the first three excitations indicate a low glucose concentration, such as ≦150 or 100 mg/dL, the sensor system may extend the analysis to greater than 7, such as greater than 8 or 10 seconds, to increase the accuracy and/or precision of the analysis.

Second, the multiple sets of calibration constants may be used to increase the accuracy and/or precision of the analysis by averaging. For example, if the target glucose measurement time is 11.5 seconds, the currents at 8.5, 10, and 11.5 seconds can be utilized to calculate the glucose concentrations using the slopes and intercepts from the corresponding calibration lines; therefore, $G_{8.5} = (i_{8.5} - Int_{8.5})/Slope_{8.5}$, $G_{10} = (i_{10} - Int_{10})/Slope_{10}$, and $G_{11.5} = (i_{11.5} - Int_{11.5})/Slope_{11.5}$. Theoretically, these three glucose values should be equivalent, differing only by random variations. Thus, the glucose values $G_{8.5}$, $G_{10}$, and $G_{11.5}$ may be averaged and the final glucose value of $(G_{8.5} + G_{10} + G_{11.5})/3$ may be calculated. Averaging the values from the calibration lines may provide a reduction in noise at the rate of $1/\sqrt{3}$).

An unexpected benefit of gated amperometric pulse sequences including relatively short excitations and relatively long relaxations, such as that depicted in FIG. 5E, is the ability to simplify calibration. While the multiple sets of calibration constants that may be obtained from the transient and contour profiles may provide an advantage to the accuracy of the analysis, a pulse sequence such as depicted in FIG. 5E may provide similar accuracy to that obtained using multiple sets of calibration constants from a single set of calibration constants. While not intending to be bound by any particular theory, this result may be attributable to the relatively long relaxation times in comparison to the short relaxations. The long relaxation times may provide a state where the average rate of measurable species conversion during the excitation is balanced by the rate of measurable species diffusion into the DBL. In this manner, the multiple sets of calibration constants may collapse into a single set and the conversion of the recorded data into an analyte concentration may be simplified by carrying out the averaging process on the recorded current data before determining the analyte concentration.

The combination of the transient current profile of each excitation and the resulting contour profiles also may be used to determine if the sensor strip has been under-filled with sample, thus allowing the user to add additional sample to the sensor strip. In addition to working and counter electrodes, conventional sensor systems may determine an under-fill condition through the use of a third electrode or electrode pair; however, the third electrode or electrode pair adds complexity and cost to the sensor system.

Conventional two electrode systems may be able to recognize that an analysis is "bad," but may not determine if the reason for the failed analysis was caused by under-fill or a defective sensor strip. The ability to determine if under-fill caused the failure of the analysis is beneficial because it may be corrected by adding additional sample to the same sensor strip and repeating the analysis, thus preventing a good strip from being discarded.

Figure 9A:
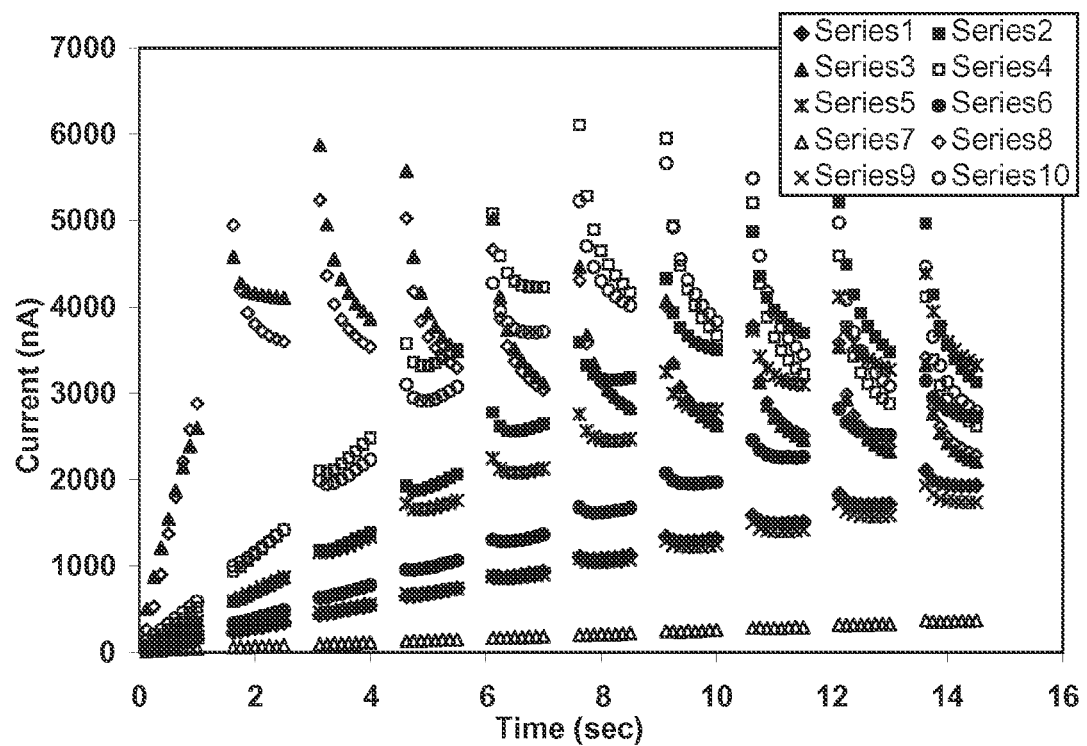
FIG. 9A depicts the transient current profiles obtained from the pulse sequence represented in FIG. 5B when a 2.0 μL sample was introduced to 10 different sensor strips.

FIG. 9A depicts the transient current profiles obtained from the pulse sequence represented in FIG. 5B for 10 analyses, each using a different sensor strip, where 2.0 μL of sample was introduced to the strip. Depending on the filling speed and the cap-gap volume of a specific sensor strip, 2.0 μL of sample may or may not be enough to fill the strip.

Figure 9B:
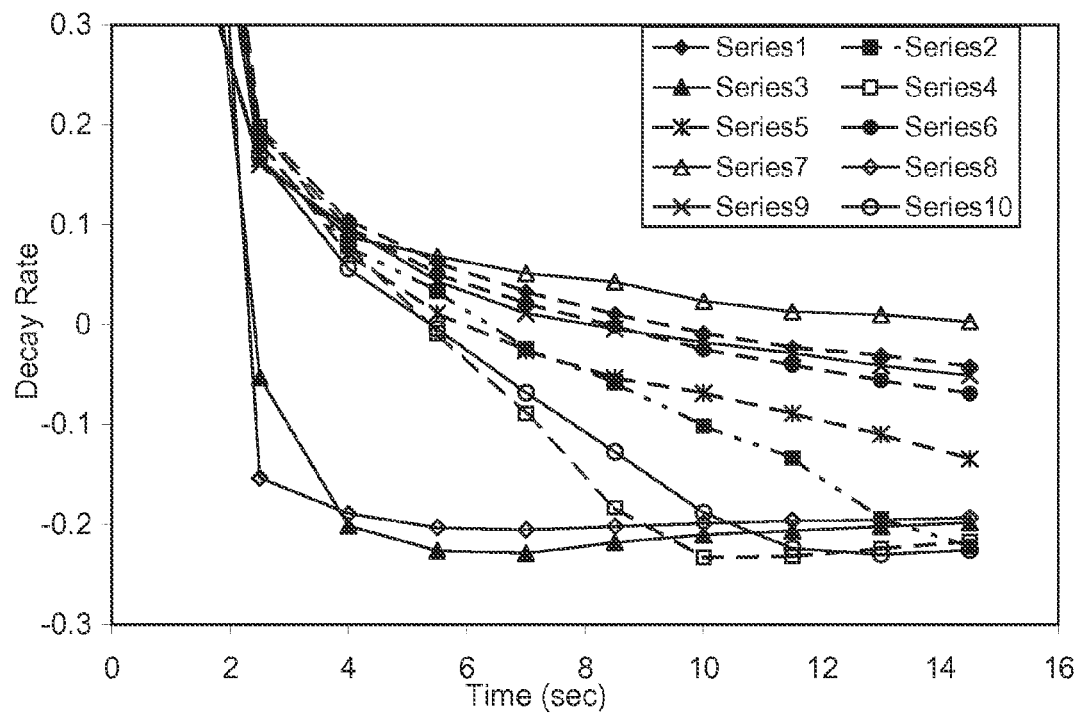
FIG. 9B depicts the profiles of the decay rate of each pulse sequence converted from FIG. 9A as a function of time.

In FIG. 9B the transient current profiles of FIG. 9A were converted to contour profiles of decay rate as a function of time. In one aspect, the decay rate may be represented as a K constant determined by either of the following equations:

$$K_1 = \frac{\ln(i_{0.125}) - \ln(i_{1.0})}{\ln(t_{0.125}) - \ln(t_{1.0})}$$

$$K_2 = \frac{\ln(i_{0.5}) - \ln(i_{1.0})}{\ln(t_{0.5}) - \ln(t_{1.0})}$$

where the 0.125, 0.5, and 1.0 values are in seconds. Thus, using the K constant of a decay process, the current profiles of FIG. 9A may be converted into the decay constant profiles of FIG. 9B.

FIG. 9B establishes that a substantial difference exists between the decay profiles of the under-filled sensors and the normal-filled sensors, especially in the time range of 3 to 7 seconds. Under-fill may be determined from the decay constant profiles by comparing the difference between the actual decay constant and a previously selected value. For example, if −0.1 is selected as the upper limit for a normal-filled sensor with regard to FIG. 9B, any K1 constant having a value lower than −0.1 determined from excitations during the 3 to 5 second time period may be considered normal-filled. Similarly, any sensor having a K1 value higher than −0.1 may be considered under-filled. In this manner, the under-fill may be determined in response to a decay rate obtained from a transient current profile.

Thus, in FIG. 9B the sensor strips represented by series 3 and 8 were sufficiently filled, while the eight sensor strips represented by series 1-2, 4-7, and 9-10 were under-filled. In this manner, the gated amperometric pulse sequences of the present invention allowed for under-fill detection in a two-electrode sensor strip, a function typically requiring a third electrode for conventional sensor systems. Furthermore, the under-fill determination was made in less than ten seconds, providing time for the measuring device to signal the user, such as by sending a signal to a light emitting device or a display, to add more sample to the strip.

Because under-fill may be determined from the transient current profiles, the same current values used to determine the presence and/or concentration of the analyte may be used to determine if an under-fill condition exists. Thus, under-fill may be determined during the multiple duty cycles of the pulse sequence without lengthening the duration of the electrochemical analysis beyond that required for concentration determination.

The combination of the transient current profile of each excitation and the resulting contour profile also may be used to determine if a change in the temperature of the sample may adversely affect the analysis. Conventional sensor systems include a thermister in the measuring device or on the strip to provide the temperature of the device or strip, respectively. While this temperature is an approximation of the sample temperature, typically, the device or strip is at a different temperature than the sample. The temperature difference between the device or strip and the sample may introduce bias into the analysis.

Figure 10:
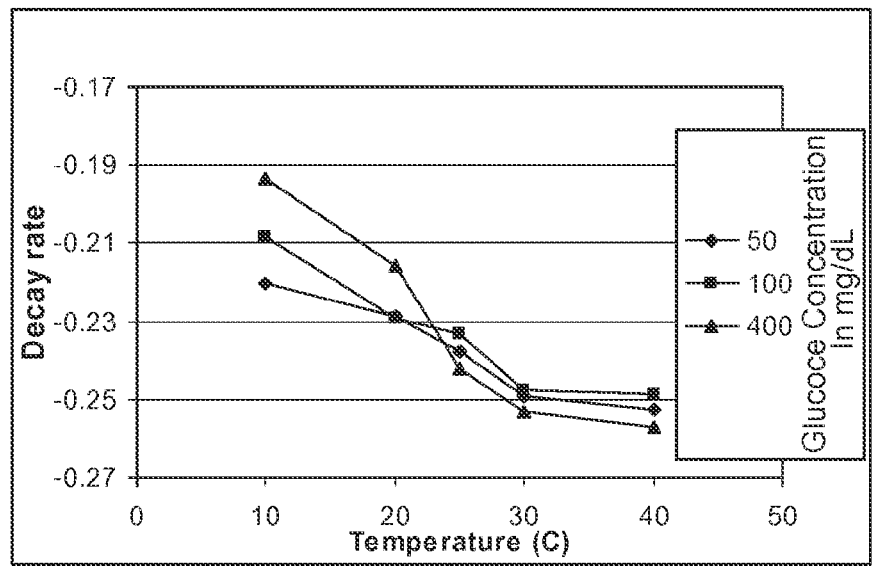
FIG. 10 plots K constants determined from a pulse sequence for glucose concentrations of 50, 100, and 400 mg/dL as a function of temperature.

By determining a decay rate, such as with a K constant as previously discussed, the temperature of the sample may be determined. FIG. 10 depicts K constants plotted as a function of temperature that were obtained from the fifth excitation of a pulse sequence for glucose concentrations of 50, 100, and 400 mg/dL. The plots establish that the decay rate increased in absolute value with increasing temperature. While not wishing to be bound by any particular theory, this phenomenon may be attributed to lower temperatures slowing down the diffusion rate of the various constituents present in the cap-gap. In this manner, the temperature of a sample may be determined in response to a decay rate obtained from a transient current profile.

Because sample temperature may be determined from the transient current profiles, the same current values used to determine the presence and/or concentration of the analyte may be used to determine the temperature of the sample. Thus, the temperature of the sample may be determined during the multiple duty cycles of the pulse sequence without lengthening the duration of the electrochemical analysis beyond that required for concentration determination.

In one aspect, the temperature of the sample may be determined by solving for K by the following equation:

$$K = \frac{\ln i_{0.125} - \ln i_{0.375}}{\ln(0.125) - \ln(0.375)}$$

where $i_{0.125}$ and $i_{0.375}$ are the currents at 0.125 and 0.375 seconds from the excitation most sensitive to temperature change, such as the excitation generating the most sensitive current decay with respect to the temperature change. $\ln(0.125)$ and $\ln(0.375)$ are the natural logarithmic terms of the times at 0.125 and 0.375 seconds, respectively. From the plot of these K constants verses temperature, as depicted in FIG. 10, the temperature of the sample may be determined by the correlation function of the plot. The correlation function may be a polynomial fit of the curve. The temperature determined from this plot may be different from the temperature of the device and may more accurately reflect the temperature of the sample.

An advantage of determining the temperature of the sample, as opposed to the device, is that the length of the analysis may be adjusted to allow sufficient time for the rehydration of a DBL to reach equilibrium, thus increasing the accuracy of the analysis. For example, if the temperature of the sample determined during the pulse sequence is at least 5 or 10° C. below ambient temperature, the pulse sequence may be lengthened, such as with additional duty cycles.

Figure 11:
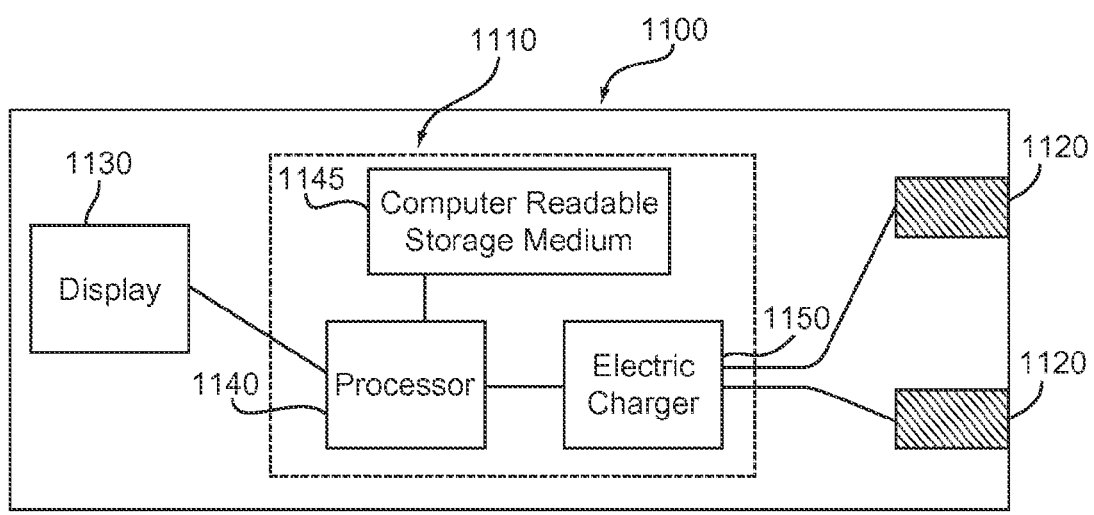
FIG. 11 is a schematic representation of a measuring device.

FIG. 11 is a schematic representation of a measuring device 1100 including contacts 1120 in electrical communication with electrical circuitry 1110 and a display 1130. In one aspect, the measuring device 1100 is portable and is adapted to be handheld and to receive a sensor strip, such as the strip 100 from FIG. 1A. In another aspect, the measuring device 1100 is a handheld measuring device adapted to receive a sensor strip and implement gated amperometric pulse sequences.

The contacts 1120 are adapted to provide electrical communication with the electrical circuitry 1110 and the contacts of a sensor strip, such as the contacts 170 and 180 of the sensor strip 100 depicted in FIG. 1B. The electrical circuitry 1110 may include an electric charger 1150, a processor 1140, and a computer readable storage medium 1145. The electrical charger 1150 may be a potentiostat, signal generator, or the like. Thus, the charger 1150 may apply a voltage to the contacts 1120 while recording the resulting current to function as a charger-recorder.

The processor 1140 may be in electrical communication with the charger 1150, the computer readable storage medium 1145, and the display 1130. If the charger is not adapted to record current, the processor 1140 may be adapted to record the current at the contacts 1120.

The computer readable storage medium 1145 may be any storage medium, such as magnetic, optical, semiconductor memory, and the like. The computer readable storage medium 1145 may be a fixed memory device or a removable memory device, such as a removable memory card. The display 1130 may be analog or digital, in one aspect a LCD display adapted to displaying a numerical reading.

When the contacts of a sensor strip containing a sample are in electrical communication with the contacts 1120, the processor 1140 may direct the charger 1150 to apply a gated amperometric pulse sequence to the sample, thus starting the analysis. The processor 1140 may start the analysis in response to the insertion of a sensor strip, the application of a sample to a previously inserted sensor strip, or in response to a user input, for example.

Instructions regarding implementation of the gated amperometric pulse sequence may be provided by computer readable software code stored in the computer readable storage medium 1145. The code may be object code or any other code describing or controlling the functionality described in this application. The data that results from the gated amperometric pulse sequence may be subjected to one or more data treatments, including the determination of decay rates, K constants, slopes, intercepts, and/or sample temperature in the processor 1140 and the results, such as a corrected analyte concentration, output to the display 1130. As with the instructions regarding the pulse sequence, the data treatment may be implemented by the processor 1140 from computer readable software code stored in the computer readable storage medium 1145.

Without limiting the scope, application, or implementation, the methods and systems previously described may be implemented using the following algorithm:

Step 1: Turn on biosensor power
Step 2: Perform biosensor self-test
Step 3: Setup to poll for application of sample to sensor
  Set ASIC polling potential to $v_{poll}$
  Set ASIC threshold level to $i_{trigger}$
  Set polling periodic timer to expire at $int_{poll}$
Step 4: Setup for assaying the sensor current
  Wait for polling periodic timer to expire
  Enable ASIC charge pump
  Enable ASIC threshold detector ($i_{trigger}$)
  Enable polling potential ($V_{poll}$)
  Select sensor channel which applies potential to sensor
  Wait for settling time $t_{poll}$
Step 5: Test if the sensor current exceeds the threshold
Step 6: Delay and test sensor current again
Step 7: Upon detection of Sample Application
  start counting time
  launch pulse sequence
Step 8: Pulse 1—Measure sensor currents $i_{1,1}$ and $i_{1,8}$
  Pulse 1 starts at time $t_{p1}$
  Set Pulse 1 duration to $d_{p1}$
  Set Pulse 1 sensor potential to $v_{p1}$
  Select sensor channel to apply potential to sensor
  At time $t_{1,1}$, measure sensor signal, save value as $AD_{S11}$
  At time $t_{1,8}$, measure sensor signal, save value as $AD_{S18}$
Step 9: Delay 1—Re-standardize electronics
  Delay 1 starts at end of $AD_2$ reading, disconnect sensor channel
  Delay 1 ends at beginning of Pulse 2
  Set potential to $V_{standardize}$
  At time $t_{c1}$, select reference resistor channel then measure signal, save value as $AD_{R1}$
  At time $t_{c2}$, select offset channel then measure signal, save value as $AD_{O1}$
  Note: sensor currents starting at Pulse 1 are calculated from the $AD_{R1}$ and $AD_{O1}$ measurements
Step 10: Pulse 2—Measure sensor currents $i_{2,1}$ and $i_{2,8}$
  Pulse 2 starts at time $t_{p2}$
  Set Pulse 2 duration to $d_{p2}$
  Set Pulse 2 sensor potential to $V_{p2}$
  Select sensor channel to apply potential to sensor
  At time $t_{2,1}$, measure sensor signal, save value as $AD_{S21}$
  At time $t_{2,8}$, measure sensor signal, save value as $AD_{S28}$
Step 11: Delay 2—
  Delay 2 starts at end of $AD_{S3}$ reading, disconnect sensor channel
  Delay 2 ends at beginning of Pulse 3
  Select offset channel to disconnect sensor
Step 12: Pulse 3—Measure sensor currents: $i_{3,1}$ and $i_{3,8}$
  Pulse 3 starts at time $t_{p3}$
  Set Pulse 3 duration to $d_{p3}$
  Set Pulse 3 sensor potential to $V_{p3}$
  Select sensor channel to apply potential to sensor
  At time $t_{3,1}$, measure sensor signal, save value as $AD_{S31}$
  At time $t_{3,8}$, measure sensor signal, save value as $AD_{S38}$
Step 13: Delay 3—$T_1$ and $i_{wet}$
  Delay 3 starts at end of $AD_{S38}$ reading, disconnect sensor channel
  Delay 3 ends at beginning of Pulse 4
  Set potential to $V^{standardize}$
  At time $t_{c3}$, select thermistor channel then measure signal, save value as $AD_{T1}$
  At time $t_{wet}$, select offset channel then measure signal, save value as $AD_{wet}$
Step 14: Pulse 4—Measure sensor currents: $i_{4,1}$, $i_{4,4}$, and $i_{4,8}$
  Pulse 4 starts at time $t_{p4}$
  Set Pulse 4 duration to $d_{p4}$
  Set Pulse 4 sensor potential to $V_{p4}$
  Select sensor channel to apply potential to sensor
  At time $t_{4,1}$, measure sensor signal, save value as $AD_{S41}$
  At time $t_{4,4}$, measure sensor signal, save value as $AD_{S44}$
  At time $t_{4,8}$, measure sensor signal, save value as $AD_{S48}$
Step 15: Delay 4—
  Delay 4 starts at end of $AD_{S48}$ reading, disconnect sensor channel
  Delay 4 ends at beginning of Pulse 5
  Select offset channel to disconnect sensor
Step 16: Pulse 5—Measure sensor currents: $i_{5,1}$, $i_{5,4}$, and $i_{5,8}$
  Pulse 5 starts at time $t_{p5}$
  Set Pulse 5 duration to $d_{p5}$
  Set Pulse 5 sensor potential to $V_{p5}$
  Select sensor channel to apply potential to sensor
  At time $t_{5,1}$, measure sensor signal, save value as $AD_{S51}$
  At time $t_{5,4}$ measure sensor signal, save value as $AD_{S54}$
  At time $t_{5,8}$, measure sensor signal, save value as $AD_{S58}$
  Disable ASIC analog functions
Step 17: Look up slope and intercept for lot calibration number
  S=Slope value for current lot calibration number
  Int=Intercept value for current lot calibration number
Step 18: Adjust slope and intercept for temperature effect
Step 19: Calculate glucose concentration at 25° C.
Step 20: Convert to target reference (plasma vs. WB reference)
Step 21: Check underfill
Step 22: Check for "Abnormal Behavior"
Step 23: If low glucose, check again for "Abnormal Behavior"
Step 25: Check for extreme glucose levels
Step 26: Display result The algorithm may have other subroutines including those to check for errors such as sample temperature and underfill conditions. The constants that may be used in the algorithm are given in Table III below. Other constants may be used.

TABLE III

| Constant | Description | Value | Units |
| --- | --- | --- | --- |
| $v_{poll}$ | polling voltage | 400 | mV |
| $int_{poll}$ | polling interval | 125 | ms |
| $t_{poll}$ | polling duration | 10 | minutes |
| $i_{trigger}$ | threshold detect trigger current | 250 | nA |
| $t_{p1}$ | pulse 1 start time | 0 | sec |
| $d_{p1}$ | pulse 1 duration | 1 | second |
| $v_{p1}$ | pulse 1 voltage level | 400 | mV |
| $t_{1,1}$ | time of sensor current reading 1 | 0.125 | sec |

TABLE III-continued

| Constant | Description | Value | Units |
|---|---|---|---|
| $t_{1,8}$ | time of sensor current reading 2 | 1.00 | sec |
| $t_{c1}$ | Offset reading time | 1.125 | sec |
| $t_{c2}$ | Reference reading time | 1.25 | sec |
| $t_{p2}$ | pulse 2 start time | 1.5 | sec |
| $d_{p2}$ | pulse 2 duration | 1 | second |
| $v_{p2}$ | pulse 2 voltage level | 200 | mV |
| $t_{2,1}$ | time of sensor current reading 3 | 1.625 | sec |
| $t_{2,8}$ | time of sensor current reading 4 | 2.50 | sec |
| $t_{p3}$ | pulse 3 start time | 3 | sec |
| $d_{p3}$ | pulse 3 duration | 1 | second |
| $v_{p3}$ | pulse 3 voltage level | 200 | mV |
| $t_{3,1}$ | time of sensor current reading 5 | 3.125 | sec |
| $t_{3,8}$ | time of sensor current reading 6 | 4.00 | sec |
| $t_{c3}$ | Thermistor reading time | 4.125 | sec |
| $t_{wet}$ | Time of wet sensor current reading | 4.25 | sec |
| $t_{p4}$ | pulse 4 start time | 4.5 | second |
| $d_{p4}$ | pulse 4 duration | 1 | second |
| $v_{p4}$ | pulse 4 voltage level | 200 | mV |
| $t_{4,1}$ | time of sensor current reading 7 | 4.625 | sec |
| $t_{4,4}$ | time of sensor current reading 8 | 5.00 | sec |
| $t_{4,8}$ | time of sensor current reading 9 | 5.50 | sec |
| $t_{p5}$ | pulse 5 start time | 6 | sec |
| $d_{p5}$ | pulse 5 duration | 1 | second |
| $v_{p5}$ | pulse 5 voltage level | 200 | mV |
| $t_{5,1}$ | time of sensor current reading 10 | 6.125 | sec |
| $t_{5,4}$ | time of sensor current reading 11 | 6.50 | sec |
| $t_{5,8}$ | time of sensor current reading 12 | 7.00 | sec |

While various embodiments of the invention have been described, it will be apparent to those of ordinary skill in the art that other embodiments and implementations are possible within the scope of the invention.

The invention claimed is:

1. An amperometric method for determining the concentration of an analyte in a sample, comprising:
applying an input signal to a sample, the input signal comprising at least 3 duty cycles within 180 seconds and each duty cycle comprising an amperometric excitation and a relaxation,
where the input signal has redox intensity of at least 0.01 over a 10 second duration of the input signal, and
where the relaxations of the at least 3 duty cycles each provide an independent diffusion and analyte reaction time during which the analyte generates measurable species;
measuring an output signal from one of the amperometric excitations having a duration from 0.01 second to 1.5 seconds, the output signal responsive to the measurable species; and
determining a concentration of an analyte in the sample in response to the measured output signal, where the determined concentration is responsive to a rate at which the measurable species is oxidized or reduced by the input signal.

2. The method of claim 1, further comprising introducing the sample to a sensor strip, the sensor strip including working and counter electrodes in electrical communication with the sample;
transferring at least one electron from the analyte in the sample to a mediator in the sensor strip; and
applying the input signal to the working and counter electrodes, where the input signal electrochemically excites the measurable species, and the measurable species is selected from the group consisting of the analyte, the mediator, and combinations thereof.

3. The method of claim 1, where the sample is whole blood including red blood cells.

4. The method of claim 1, where the measurable species is a mediator selected from the group consisting of organotransition metal complexes, coordination complexes, electro-active organic molecules, and combinations thereof.

5. The method of claim 1, where the excitation from which the output signal is determined has a duration from 0.1 to 1.2 seconds.

6. The method of claim 1, the input signal comprising from 4 to 8 duty cycles applied within 3 to 16 seconds.

7. The method of claim 1, the input signal comprising from 3 to 18 duty cycles applied within 30 seconds.

8. The method of claim 1, further comprising:
exciting the measurable species internal to a diffusion barrier layer having an average initial thickness from 1 to 30 micrometers, the diffusion barrier layer including a polymeric binder layer that is partially water-soluble; and
substantially excluding from excitation the measurable species external to the diffusion barrier layer, where the diffusion barrier layer provides an internal porous space to contain and isolate a portion of the measurable species from the sample.

9. The method of claim 1, where the measured output signal is the greatest last in time current value obtained from the duty cycles.

10. The method of claim 1, further comprising determining the concentration of the analyte in response to a current profile of the measured output signal when a relatively constant diffusion rate of the measurable species is reached.

11. The method of claim 1, where the measured output signal comprises at least one current profile and the concentration of the analyte in the sample is determined in response to the at least one current profile.

12. The method of claim 11, where the excitations of the duty cycle have a duration in the range of 0.1 second through 1.5 second and the duty cycles have a pulse interval in the range of about 0.2 second through about 3.5 seconds.

13. The method of claim 11, where the excitations of the duty cycles have a duration in the range of about 0.4 second through about 1.2 second and the duty cycles have a pulse interval in the range of about 0.6 second through about 3.7 seconds.

14. The method of claim 11, where the current profile includes a transient decay and the analyte concentration is determined from the transient decay.

15. The method of claim 11, further comprising establishing multiple sets of calibration constants in response to the output signal.

16. The method of claim 15, further comprising determining the number of duty cycles in the input signal in response to the multiple sets of calibration constants.

17. The method of claim 15, further comprising:
determining the concentration of the analyte in the sample in response to each set of calibration constants; and
averaging the concentrations of the analyte from the sets of the calibration constants.

18. The method of claim 11, further comprising determining the temperature of the sample contained by a sensor strip in response to a decay rate of the current profile.

19. The method of claim 11, further comprising determining when a sensor strip is under-filled in response to the current profile.

20. The method of claim 19, further comprising determining when the sensor strip is under-filled when a decay rate of the current profile is less than a selected value.

21. The method of claim 20, where the selected value is −0.1.

22. The method of claim 1, where the relaxation has a duration from 0.1 second to 3 seconds.

23. The method of claim 1, further comprising filling a cap-gap of a sensor strip with the sample while expelling previously contained air through a vent before applying the input signal to the sample.

24. The method of claim 23, where the cap-gap is formed with a lid including the vent.

\* \* \* \* \*